United States Patent
Mutharasan et al.

(10) Patent No.: US 8,778,446 B2
(45) Date of Patent: *Jul. 15, 2014

(54) FLOW CELLS FOR PIEZOELECTRIC CANTILEVER SENSORS

(75) Inventors: Rajakkannu Mutharasan, West Chester, PA (US); Gossett Augustus Campbell, Conshohocken, PA (US)

(73) Assignee: Drexel University, Philadelphia, PA (US)

(*) Notice: Subject to any disclaimer, the term of this patent is extended or adjusted under 35 U.S.C. 154(b) by 1482 days.

This patent is subject to a terminal disclaimer.

(21) Appl. No.: 11/836,290

(22) Filed: Aug. 9, 2007

(65) Prior Publication Data
US 2008/0034840 A1 Feb. 14, 2008

Related U.S. Application Data

(60) Provisional application No. 60/821,883, filed on Aug. 9, 2006.

(51) Int. Cl.
C23C 14/54 (2006.01)

(52) U.S. Cl.
USPC ...... 427/10; 435/286.5; 435/287.5; 73/61.79; 427/2.11

(58) Field of Classification Search
None
See application file for complete search history.

(56) References Cited

U.S. PATENT DOCUMENTS

| | | | |
|---|---|---|---|
| 3,560,099 A * | 2/1971 | Boes et al. | 356/246 |
| 4,186,599 A | 2/1980 | Frick | |
| 4,791,818 A | 12/1988 | Wilde et al. | |
| 5,116,759 A * | 5/1992 | Klainer et al. | 435/287.2 |
| 5,583,300 A | 12/1996 | Green et al. | |
| 5,719,324 A | 2/1998 | Thundat et al. | 73/24.01 |
| 5,770,462 A * | 6/1998 | Molloy | 436/527 |
| 6,170,981 B1 | 1/2001 | Regnier et al. | |
| 6,336,366 B1 | 1/2002 | Thundat et al. | 73/514.34 |
| 6,543,274 B1 | 4/2003 | Herrmann et al. | |
| 6,880,402 B1 | 4/2005 | Couet et al. | |
| 7,105,301 B2 | 9/2006 | Su et al. | |
| 7,409,851 B2 | 8/2008 | Llic et al. | |
| 7,458,265 B2 | 12/2008 | Shih et al. | |
| 7,504,219 B2 | 3/2009 | Bickmore, Jr. et al. | |
| 7,892,759 B2 | 2/2011 | Mutharasan et al. | |
| 8,171,795 B1 | 5/2012 | Mutharasan et al. | |
| 2002/0012616 A1 * | 1/2002 | Zhou et al. | 422/130 |

(Continued)

FOREIGN PATENT DOCUMENTS

WO WO 2005/043126 5/2005

OTHER PUBLICATIONS

Campbell et al. Sensing of liquid level at micron resolution using self-excited millimeter-sized PZT-cantilever, Sensors and Actuators A (2005) 122:326-334.*

(Continued)

*Primary Examiner* — Melanie Y Brown
*Assistant Examiner* — Rebecca Martinez
(74) *Attorney, Agent, or Firm* — Baker & Hostetler LLP

(57) ABSTRACT

Flow cells configured for piezoelectric millimeter-sized cantilever sensors provide direct, sensitive detection of analytes in fluid media. The flow cells comprise a flow inlet and a flow outlet positioned to cause sample flow past a sensing surface of the cantilever sensor. The flow cell is configured for millimeter-sized cantilever sensors. The geometry of the flow cell influences the sample flow and thus the interaction of the flow with the cantilever sensor.

38 Claims, 29 Drawing Sheets

(56) References Cited

U.S. PATENT DOCUMENTS

| | | | |
|---|---|---|---|
| 2002/0092340 A1* | 7/2002 | Prater et al. | 73/24.02 |
| 2003/0215816 A1 | 11/2003 | Sundararrajan et al. | |
| 2004/0115711 A1 | 6/2004 | Su et al. | |
| 2004/0197845 A1* | 10/2004 | Hassibi et al. | 435/8 |
| 2005/0112621 A1 | 5/2005 | Kim et al. | |
| 2006/0065046 A1* | 3/2006 | Battiston et al. | 73/61.79 |
| 2011/0138915 A1 | 6/2011 | Mutharasan et al. | |

OTHER PUBLICATIONS

U.S. Appl. No. 11/659,919, filed Jan. 23, 2007, Mutharasan, et al.

U.S. Appl. No. 11/747,183, filed May 10, 2007, Mutharasan, et al.

U.S. Appl. No. 60/746,951, filed May 10, 2006, Mutharasan, et al.

U.S. Appl. No. 60/761,172, filed Jan. 23, 2006, Mutharasan, et al.

U.S. Appl. No. 60/807,020, filed Jul. 11, 2006, Mutharasan, et al.

Campbell, G.A., et al., "Detection of *Bacillus anthracts* spores and a model protein using PEMC sensors in a flow cell at 1 mL/MIN," Biosensors and Bioelectronics, 1-29, 2005.

Campbell, G.A., et al., "A method of measuring *Escherichia coli* 0157:h7 AT 1 CELL/M1 IN 1 liter sample using antibody functionalized piezoelectric-excited millimeter-sized cantilever," Environmental Science & Technology, 1-24, 2006.

Campbell, G.A., et al., "PEMC sensor's mass change sensitivity in 20 PG/HZ under liquid immersion," Biosensors and Bioelectronics, 1-28, 2005.

Campbell, G.A., et al., "Piezoelectric-excited millimeter-sized cantilever (PEMC) sensors measure albumin interaction with self-assembled monolayers of alkanethiols having different functional head groups," J of Analytical Chem., 1-27, 2005.

Campbell, G.A., et al., "Detection and quantification of proteins using self-excited PZT-glass millimeter-sized cantilever," Biosensors and Bioelectronics, 26-36, 2005.

Campbell, G.A., "Piezoelectric-excited millimeter-sized cantilever (PEMC) sensors detect *Bacillus anthracis* at 300 spores/mL," Biosensors and Bioelectronics, 37-45, 2005.

Campbell, G.A., et al., "Kinetics of *Bacillus anthracis* spore binding to antibody functionalized PEMC sensors in presence of *Bacillus thuringiensis* and *Bacillus cereus*," J. Publications, Am. Chem. Soc., 25 pages, 2006.

Campbell, G.A., et al., "*Escherichia coli* O157:H7 detection limit a millimeter-sized PZT cantilever sensors in 700 cells/mL," Analytical Sci., 11-13, 2005.

Campbell, G.A., et al., "Detection of pathogen *Escherichia coli* O157:H7 using self-excited PZT-glass microcantilevers," Biosensors and Bioelectronics, 14-25, 2004.

Campbell, G.A., "Detection of *Staphylococcus* enterotoxin B at pictogram levels using piezoelectric-excited millimeter-sized cantilever sensors," Submitted on-line to J. of Analytical Chem, 1-24, 2006.

Campbell, G.A., et al., "Detect of *Escherichia coli* O157:H7 in ground beef samples using piezoelectric excited millimeter-sized cantilever (PEMC) sensors," Biosensors and Bioelectronics, 2006, 1-7.

Carr, D.W., et al., "Fabrication of nanoelectromechanical systems in single crystal silicon using silicon on insulator substrates and electron beam lithography," J. Vac. Sci. Technology, B, 5(6), 2760-2763, 1997.

Wilson, L., et al., "Viscosity and density values from excitation level response of piezoelectric-excited cantilever sensors," Sensors and Actuators A, 2007, 138, 44-51.

\* cited by examiner

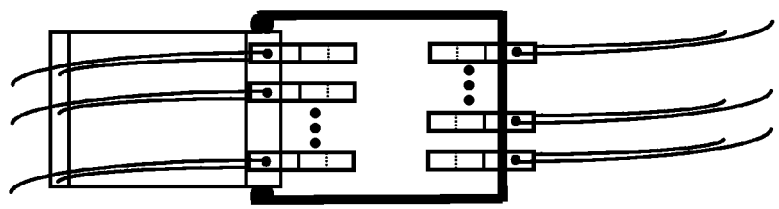
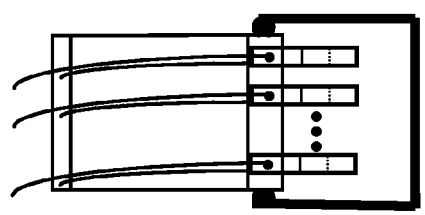
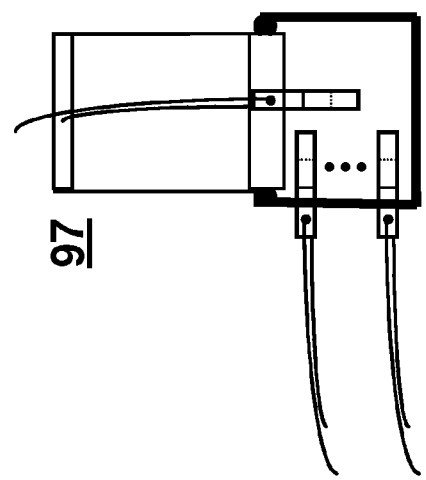
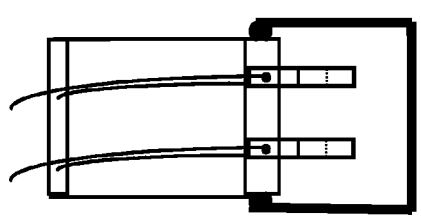
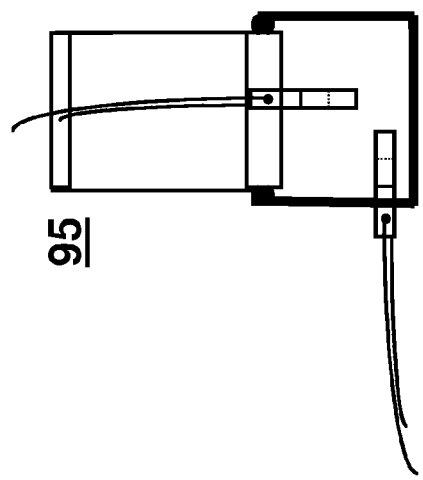
FIGURE 14

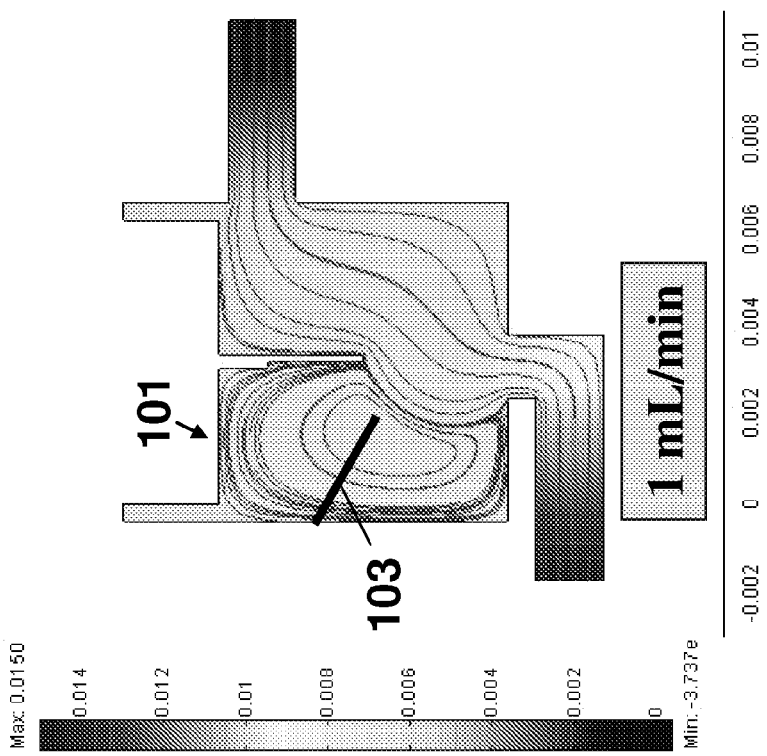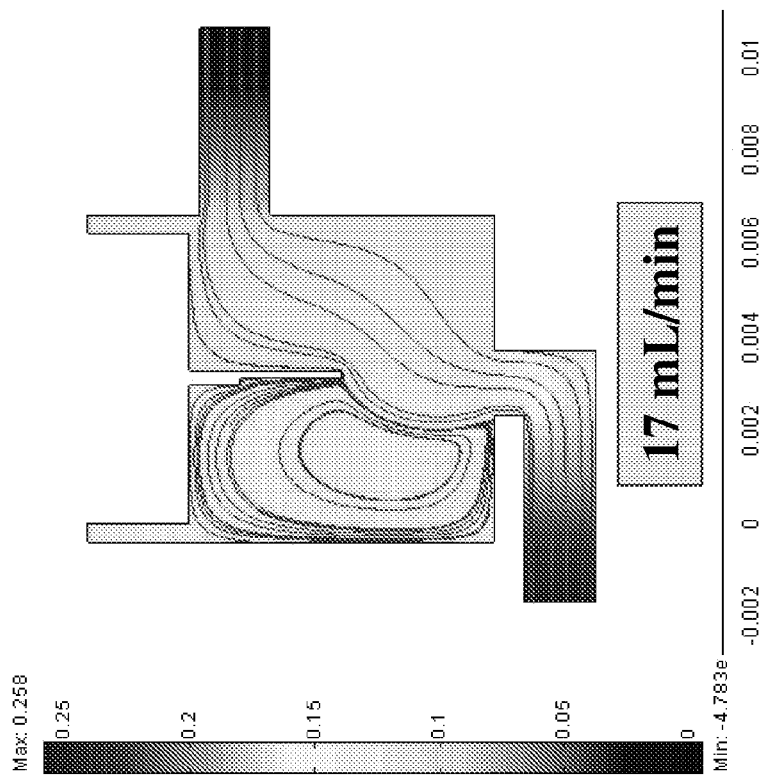
FIGURE 20

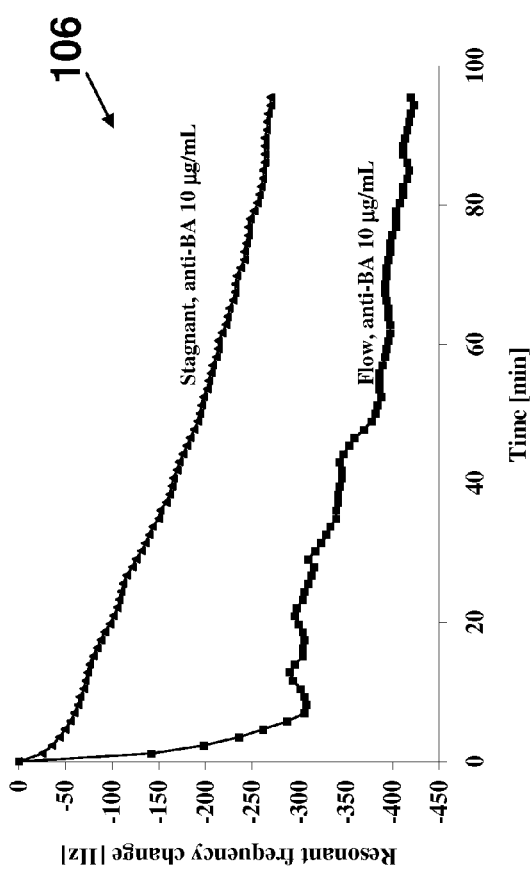
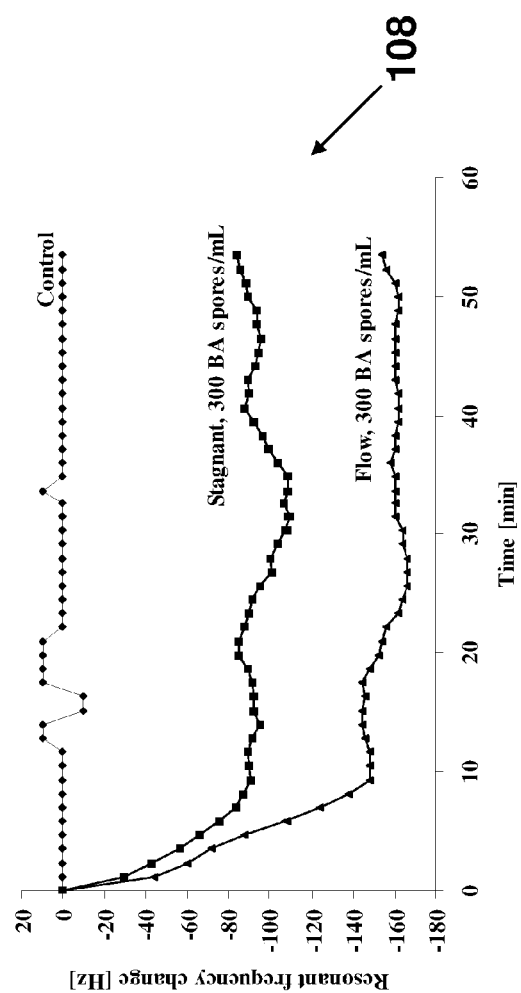
FIGURE 23

FLOW CELLS FOR PIEZOELECTRIC CANTILEVER SENSORS

CROSS REFERENCE TO RELATED APPLICATIONS

The present application claims priority to U.S. Provisional Patent Application No. 60/821,883, entitled "FLOW CELLS FOR PIEZOELECTRIC CANTILEVER SENSORS," filed Aug. 9, 2006, which is hereby incorporated by reference in its entirety.

TECHNICAL FIELD

The technical field generally relates to detection of materials in a medium such as a fluid (liquid or gas). More particularly, the technical field relates to flow cells for use in conjunction with piezoelectric cantilever sensors for detecting materials in a medium.

BACKGROUND

Sensors that rely on mechanical resonance such as quartz crystal microbalance (QCM) sensors, microcantilever sensors, and plasma resonance sensors (SPR) are commonly used in flow cells. A flow cell is a vessel in which a sensor is placed to detect material in a medium. Typically, the medium is pumped through the flow cell. Thus, the medium flows through the cell, and hence the moniker flow cell. Typically flow rates of the medium in flow cells utilizing mechanical resonance sensors are on the order of micro-liters per minute (μL/min). For example, the recommended liquid flow rate for use in instrument grade quartz crystal microbalance QCM sensors is 200 μL/min. Lower flow rates of about 33 μL/min are typically used with other microcantilever sensors.

In general, performance of both QCM and microcantilever sensors deteriorates at high flow rates. This can present a problem when the sample volume of the medium is large and the amount of target material (material to be detected) in the medium is low. For example, the tolerable level for *Cryptosporidium* and *Giardia* is 0.2 cells per liter of drinking water. Thus, using a typical QCM and microcantilever sensor to test a source of drinking water for parasites, such as *Cryptosporidium* (a parasite known to cause diarrhea) or *Giardia* (a parasite known to infect the intestinal tract), is neither effective or practicable without a concentrating step.

SUMMARY

Flow cells are configured for use with millimeter sized piezoelectric cantilever sensors to detect target material (analyte) in fluid media. In example configurations, the flow cells include a flow inlet and a flow outlet positioned to cause the medium potentially containing an analyte (referred to as a sample), to flow past a sensing surface of the cantilever sensor. The flow cell is adapted for millimeter-sized cantilever sensors. The geometry of the flow cell influences the sample flow and thus the interaction of the flow with the cantilever sensor. The flow characteristics resulting from the flow cell configurations enhance the ability of the piezoelectric cantilever sensor positioned therein to detect changes in mass accumulated on the sensing surface of the sensor.

BRIEF DESCRIPTION OF THE DRAWINGS

The foregoing summary, as well as the following detailed description, is better understood when read in conjunction with the appended drawings. For the purpose of illustrating a flow cell configured for a piezoelectric-excited millimeter-sized cantilever (PEMC) sensor, there is shown in the drawings exemplary constructions thereof; however, a flow cell configured for a PEMC sensor is not limited to the specific methods and instrumentalities disclosed.

FIG. 14 is an illustration of a cross sectional view of example flow cell configurations comprising multiple PEMC sensors.

FIG. 20 is yet another graph illustrating a pressure map and velocity field in a flow cell at the various flow rates.

FIG. 23 is another example graph illustrating the change in the resonance frequency of a PEMC sensor in a flow cell as a function of time.

DETAILED DESCRIPTION OF ILLUSTRATIVE EMBODIMENTS

Piezoelectric-excited millimeter-sized cantilever (PEMC) sensors as described herein are extremely sensitive detectors capable of detecting small changes in mass due to material accumulating on a detection surface of the sensor. The flow cells described herein are compatible with, and designed to utilize, these PEMC sensors. The flow cell configurations allow flow rates higher than 17 milliliters per minute (mL/min) while maintaining detection performance and without harming the PEMC sensor. The flow cells are configured for use with PEMC sensors at frequencies up to 5 MHz. The ability to detect target materials (analytes) is superior under flow conditions, as compared to stagnant conditions. The sample flow enhances binding of target analytes to the PEMC sensor surface. Additionally, the herein described flow cells have application to liquid chromatography utilizing a PEMC sensor. Liquid chromatography is an analytical instrument that has as its first step a separation column followed by a detector. In this application, the flow cell is utilized to separate analyte from the medium and the PEMC sensor is utilized to detect/measure analyte.

When the target analyte is present at very low concentrations, on the order of fg/mL, for example, the sample can be contacted with the sensor surface in a recirculation mode enhancing binding to the sensor surface, thus improving detection sensitivity. In this regard, the flow cell enhances detection. When the target antigen comprises particulate matter, such as a spore, for example, the flow prevents settling of the analyte, thereby enhancing contact with sensor surface and the resulting detection. Sensor performance depends, in part upon the transport of the analyte to sensor surface and the subsequent binding to the sensor surface. The former is strongly influenced by the flow rate (and/or local velocity of the fluid), and the orientation of the sensing surface with respect to the flow. The flow cell enhances the transport of analyte to the sensor surface.

The flow cells described herein are configured to utilize PEMC sensors for detection of analytes under full fluid (liquid and/or gas) immersion and flow conditions. In this manner, large sample volumes can be handled expeditiously.

Sensor Overview

Figure 1:
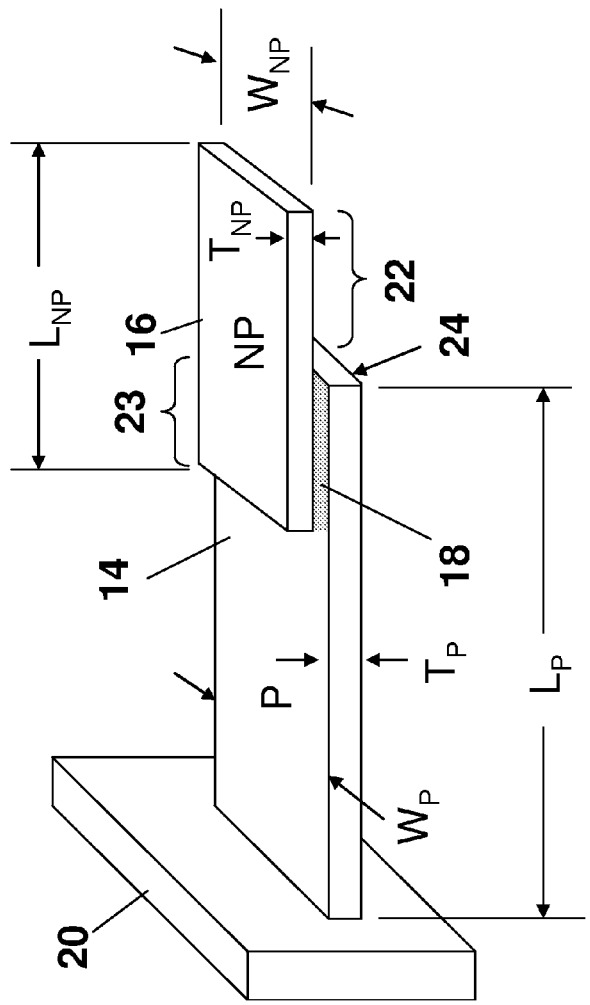
FIG. 1 is an illustration of an example configuration of a self-exciting, self-sensing piezoelectric cantilever sensor.

FIG. 1 is an illustration of an example PEMC sensor 12. The PEMC sensor 12 comprises a piezoelectric portion 14 and a non-piezoelectric portion 16. Piezoelectric portions are labeled with an uppercase letter p ("P"), and non-piezoelectric portions are labeled with the uppercase letters np ("NP"). The PEMC sensor 12 depicts an embodiment of an unanchored, overhang, PEMC sensor. The PEMC sensor 12 is termed "unanchored" because the non-piezoelectric layer 16 is not attached to the base portion 20. The PEMC sensor 12 is termed, "overhang" because the non-piezoelectric layer 16 extends beyond the distal tip 24 of the piezoelectric layer 14 to create an overhanging portion 22 of the non-piezoelectric layer 16. The piezoelectric portion 14 is coupled to the non-piezoelectric portion 16 via adhesive portion 18. The piezoelectric portion 14 and the non-piezoelectric portion overlap at region 23. The adhesive portion 18 is positioned between the overlapping portions of the piezoelectric portion 14 and the non-piezoelectric portion 16. The piezoelectric portion 14 is coupled to a base portion 20.

The PEMC sensor 12 provides the ability to detect and measure extremely small amounts of an analyte. The PEMC sensor 12 can be utilized to detect and measure an analyte immersed in a liquid and an analyte contained in a gas or vacuum. In various example configurations, the PEMC sensor 12 comprises at least one piezoelectric layer 14 and at least one non-piezoelectric layer 16, wherein the piezoelectric layer 14 is coupled to the non-piezoelectric layer 16. The piezoelectric layer 14, the non-piezoelectric layer 16, or both can be coupled to at least one base 20. The piezoelectric layer and the non-piezoelectric layer can be of varying widths ($W_P$), lengths ($L_P$, $L_{NP}$), and thicknesses ($T_P$, $T_{NP}$).

The PEMC sensor 12 is utilizable to determine the mass of an analyte accumulated thereon. In an example embodiment, a portion of the PEMC sensor is placed in a medium (e.g., liquid, gas, vacuum). While in the medium, a resonance frequency of the PEMC sensor is measured and compared to a baseline resonance frequency. The difference in the measured resonance frequency and the baseline resonance frequency is indicative of an amount of mass of analyte accumulated (e.g., bound, adsorbed, absorbed) on the PEMC sensor.

Analytes can be directly or indirectly bound to the surface of the non-piezoelectric portion 16 of the PEMC sensor 12. Binding of an analyte to the non-piezoelectric portion 16 of the PEMC sensor 12 results in a change in mass of the PEMC sensor 12, a change in stiffness of the PEMC sensor 12, or a combination thereof. The changes in mass and/or stiffness are measurable as changes in resonance frequency, and can be monitored and measured by an appropriate analysis device, such as an operational amplifier, an impedance analyzer, a network analyzer, an oscillator circuit, or the like, for example. Resonance frequency changes, wherein at least a portion of the PEMC sensor 12 is immersed in a liquid, are detectable and measurable. Resonance frequency changes, wherein at least a portion of the PEMC sensor is immersed in a gas or a vacuum, also are detectable and measurable.

The PEMC sensor 12 is operateable at high frequencies, such as, on the order of 0.1 MHz. to 6 MHz, for example. At these high frequencies, a Q factor (the ratio of the resonance peak frequency relative to the resonance peak width at half peak height), on the order of 10 to 100, under liquid immersion is obtainable. The PEMC sensor 12 is operateable at relative high frequencies in liquid media, gas media, and a vacuum. The PEMC sensor 12 thus provides extreme sensitivity to mass changes. The PEMC sensor 12 is especially suitable for analytes that are present at very low concentrations in media such as in body fluids, water, and food materials, for example.

The PEMC sensor 12 provides the ability to detect changes in mass accumulated thereon as small as 1 femtogram/Hz ($1\times10^{-18}$ grams/Hertz) or less when immersed in a liquid media. Thus, with respect to detecting changes in mass, the PEMC sensor 12 is approximately 1 billion times more sensitive than a 5 MHz quartz crystal micro-balance sensor, approximate one million times more sensitive than standard analytical instruments, and nearly a billion-fold more sensitive than conventional assay method known as enzyme-linked immunosorption assay (ELISA).

The PEMC sensor 12 permits detection of extremely small concentrations of analyte that bind to it. Utilizing the PEMC sensor, pathogens and proteins are detectable at concentrations as low as a few pathogens/mL and, for proteins of average size (60 kilo-Daltons, kDa), at less than 10 fg/mL. Furthermore, any analyte that binds to an organic or inorganic functional group on the sensor is detectable. The PEMC sensor 12 is operable in media having relatively high flow rates. The PEMC sensor 12 is operable in media having flow rates of 0.5 to 10.0 mL/minute, which is approximately 1000 times the flow rate used successfully with known bending mode micro-cantilevers.

Various example applications of the piezoelectric cantilever include the detection of bioterrorism agents, such as *Bacillus anthracis*, the detection of food-borne pathogens, such as *E. coli*, the detection of pathogens in food and water, the detection of certain cell types in body fluids (e.g., circulating tumor cells), the detection of biomarkers in body fluids (e.g., proteins that mark specific pathophysiology-alpha-fetoprotein, beta-2-microglobulin, bladder tumor antigen, breast cancer marker CA-15-3, and other CAs (cancer antigens), calcitonin, carcinoembryonic antigen, and others), the detection of markers of explosives such as trinitrotoluene (TNT), the presence of dinitrotoluene (DNT), the detection of airborne and waterborne toxins, and the measurement of viscosity and density of fluids (liquids and gases). The PEMC sensor also can be used for the detection of biological entities at attogram levels, and for the detection of protein-protein interactions, both steady state and kinetic.

Pathogens, such as *E-coli* for example, are detectable utilizing the PEMC sensor 12. Detection of a model protein, lipoprotein, DNA, and/or RNA at a concentration less than 1.0 femtogram per mL ($10^{-15}$ grams) and pathogens at less than 1 pathogen/mL, respectively is achievable by measuring directly in liquid using the PEMC sensor immobilized with antibodies specific to the target analyte at a frequency of about 5 MHz. The PEMC sensor 12 is capable of detecting a target analyte without false positives or negatives even when contaminating entities are present. The PEMC sensor 12 is particularly advantageous when utilized with a raw sample, and no preparation, concentrating step, and/or enrichment of any type. Detection of an analyte utilizing the PEMC sensor 12 can be conducted directly in raw samples under flow conditions, greater than 15 mL/minute, for example. This sensitivity is approximately one million times more sensitive than the sensitivity associated with ELISA.

As described below, the sensitivity of the PEMC sensor 12 is due in part to the geometric design thereof. The relative lengths and widths of the piezoelectric layer 14 and the non-piezoelectric layer 16, of the PEMC sensor 12 determine the sensitivity, and also the shape of the peak of the frequency spectrum provided by the PEMC sensor 12. As described in more detail below, the PEMC sensor 12 comprises a piezoelectric layer 14 and a non-piezoelectric layer 16 coupled together.

The sensitivity of the PEMC sensor 12 is due in part to utilizing the piezoelectric layer 14 of the PEMC sensor 12 for both actuation and sensing of the electromechanical properties of the piezoelectric layer 14 of the PEMC sensor 12. At resonance, the oscillating cantilever concentrates stress in the piezoelectric layer 14 toward the base portion 20 of the PEMC sensor 12. This results in an amplified change in the resistive component of the piezoelectric layer 14 and a large shift in resonance frequency. Directing this stress to a portion of the piezoelectric layer 14 having a low bending modulus allows for exploitation of the associated shift in resonance frequency to detect extremely small changes in mass of the PEMC sensor 12. For example, if both the piezoelectric layer and the non-piezoelectric layer of a piezoelectric cantilever sensor are anchored at the same end (e.g., potted in epoxy), the sensor is less sensitive to changes in mass because the bending stress in the sensing piezoelectric layer proximal to the anchored end is lower compared to the case when only the piezoelectric layer is anchored. This is because the bending modulus of the two combined layers is higher than the case of anchoring the piezoelectric layer only. Bending modulus is the product of elastic modulus and moment of inertia about the neutral axis. And, moment of inertia is proportional to the cube power of thickness.

The piezoelectric portion 14 can comprise any appropriate material such as lead zirconate titanate, lead magnesium niobate-lead titanate solid solutions, strontium lead titanate, quartz silica, piezoelectric ceramic lead zirconate and titanate (PZT), piezoceramic-polymer fiber composites, or the like, for example. The non-piezoelectric portion 16 can comprise any appropriate material such as glass, ceramics, metals, polymers and composites of one or more of ceramics, and polymers, such as silicon dioxide, copper, stainless steel, titanium, or the like, for example.

The PEMC sensor 12 can comprise portions having any appropriate combination of dimensions. Further, physical dimensions can be non-uniform. Thus, the piezoelectric layer and/or the non-piezoelectric layer can be tapered. For example, the length (e.g., $L_P$ in FIG. 1) of the piezoelectric portion (e.g., piezoelectric portion 14) can range from about 0.1 to about 10 mm. The length (e.g., $L_{NP}$ in FIG. 1) of the non-piezoelectric portion (e.g., non-piezoelectric portion 16) can range from about 0.1 to about 10 mm. The overlap region (e.g., overlap region 23) can range from about 0.1 to about 10 mm in length. The width (e.g., $W_P$ in FIG. 1) of the piezoelectric portion (e.g., piezoelectric portion 14), and the width (e.g., $W_{NP}$ in FIG. 1) of the non-piezoelectric portion (e.g., non-piezoelectric portion 16), can range from about 0.1 mm to about 4.0 mm. The width (e.g., $W_P$ in FIG. 1) of the piezoelectric portion can differ from the width (e.g., $W_{NP}$ in FIG. 1) of the non-piezoelectric portion as well. The thickness of the (e.g., $T_P$ in FIG. 1) of the piezoelectric portion (e.g., piezoelectric portion 14), and the thickness (e.g., $T_{NP}$ in FIG. 1) of the non-piezoelectric portion (e.g., non-piezoelectric portion 16), can range from about 0.1 mm to about 4.0 mm. The thickness (e.g., $T_P$ in FIG. 1) of the piezoelectric portion also can differ from the thickness (e.g., $T_{NP}$ in FIG. 1) of the non-piezoelectric portion.

Figure 2:
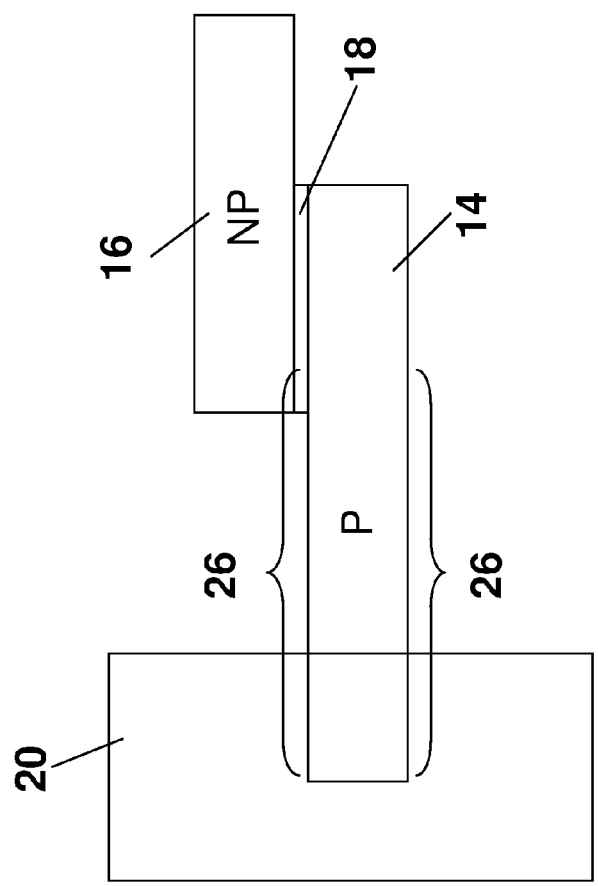
FIG. 2 is a cross-sectional view of an example self-exciting, self-sensing piezoelectric cantilever sensor depicting electrode placement regions for electrodes operationally associated with the piezoelectric layer.
Figure 3:
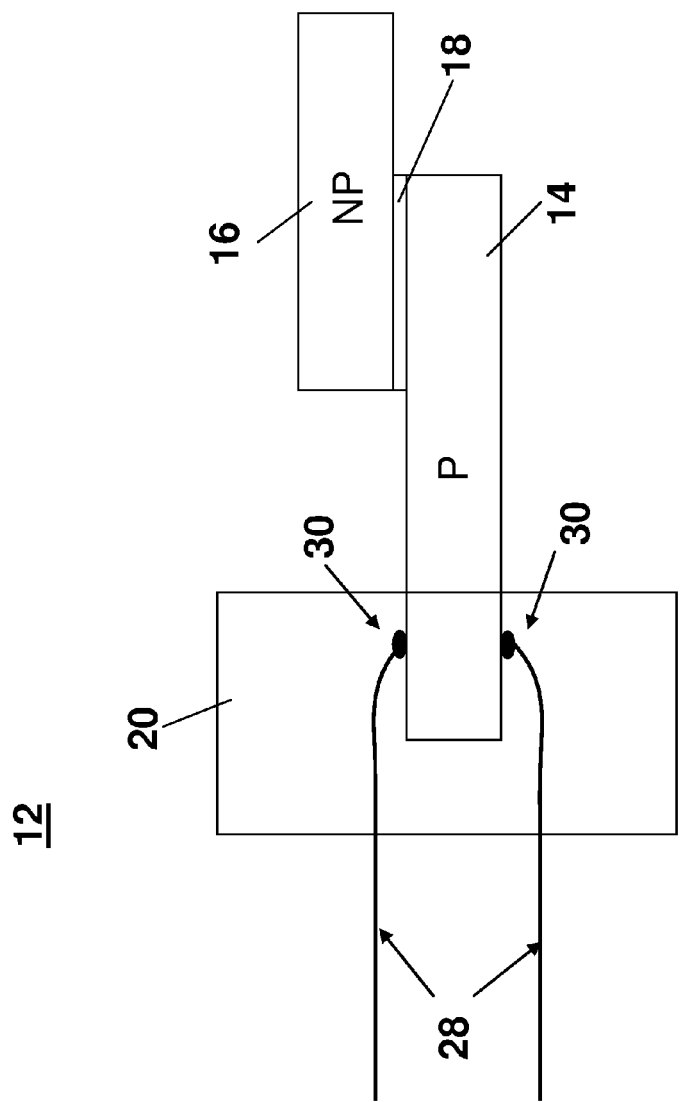
FIG. 3 is a cross-sectional view of an example self-exciting, self-sensing piezoelectric cantilever sensor showing depicting example electrode placement within a base portion of the self-exciting, self-sensing piezoelectric cantilever sensor.
Figure 4:
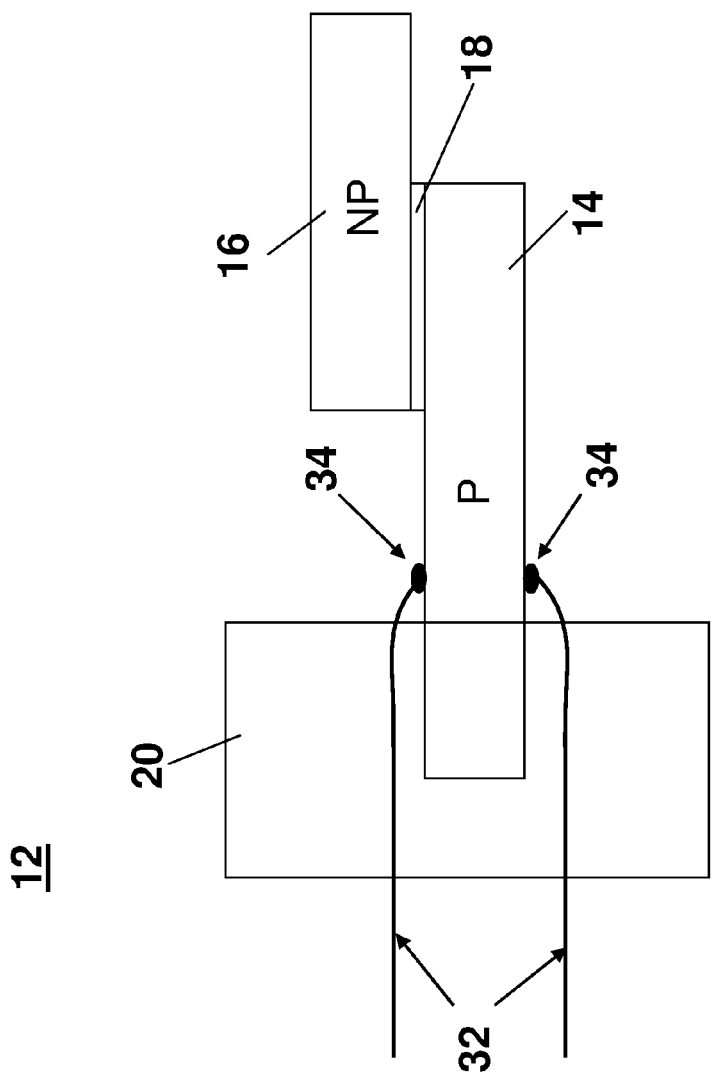
FIG. 4 is a cross-sectional view of an example self-exciting, self-sensing piezoelectric cantilever sensor showing depicting example electrode placement not within a base portion of the self-exciting, self-sensing piezoelectric cantilever sensor.

FIG. 2 is a cross-sectional view of the PEMC sensor 12 depicting electrode placement regions 26 for electrodes operationally associated with the piezoelectric portion 14. Electrodes can be placed at any appropriate location on the piezoelectric portion of the PEMC sensor 12 as indicated by brackets 26. For example, as shown in FIG. 3, electrodes 28 can be coupled to the piezoelectric portion 14 within the base portion 20. Or, as depicted in FIG. 4, electrodes 32 can be coupled to the piezoelectric portion 14 at any location not within the base portion 20. Electrodes need not be placed symmetrically about the piezoelectric portion 14. In an example embodiment, one electrode can be coupled to the piezoelectric portion 14 within the base portion 20 and the other electrode can be coupled to the piezoelectric portion 14 not within the base portion 20. Electrodes, or any appropriate means (e.g., inductive means, wireless means), can be utilized to provide an electrical signal to and receive an electrical signal from the piezoelectric portion 14. In an example embodiment, electrodes can be coupled to the piezoelectric portion 14 via a bonding pad or the like (depicted as elements 30 in FIG. 3 and elements 34 in FIG. 4). Example bonding pads can comprise any appropriate material (e.g., gold, silicon oxide) capable of immobilization of a receptor material and/or an absorbent material appropriate for use in chemical sensing or for bio-sensing.

Electrodes can be placed at any appropriate location on the PEMC sensor 12. In an example embodiment, electrodes are operatively located near a location of concentrated stress in the piezoelectric layer 14. As described above, the sensitivity of the PEMC sensor is due in part to advantageously directing (concentrating) the stress in the piezoelectric layer 14 and placing electrodes proximate thereto. The configurations of the PEMC sensor described herein (and variants thereof) tend to concentrate oscillation associated stress in the piezoelectric layer 14. At resonance, in some of the configurations of the PEMC sensor 12, the oscillating cantilever concentrates stress in the piezoelectric layer 14 toward the base portion 20. This results in an amplified change in the resistive component of the piezoelectric layer 14 and a large shift in phase angle at resonance frequency at the locations of high stress. Directing this stress to a portion of the piezoelectric layer 14 having a low bending modulus allows for exploitation of the associated shift in resonance frequency to detect extremely small changes in mass of the PEMC sensor 12. Thus, in example configurations of the PEMC sensor 12, the thickness of the piezoelectric layer 14 located near the base portion 20 is thinner than portions of the piezoelectric layer 14 further away from the base portion 20. This tends to concentrate stress toward the thinner portion of the piezoelectric layer 14. In example configurations, electrodes are located at or near the locations of the oscillation associated concentrated stress near the base portion of the PEMC sensor. In other example configurations of the PEMC sensor electrodes are positioned proximate the location of concentrated stress in the piezoelectric layer regardless of the proximity of the concentrated stress to a base portion of the PEMC sensor.

Figure 5:
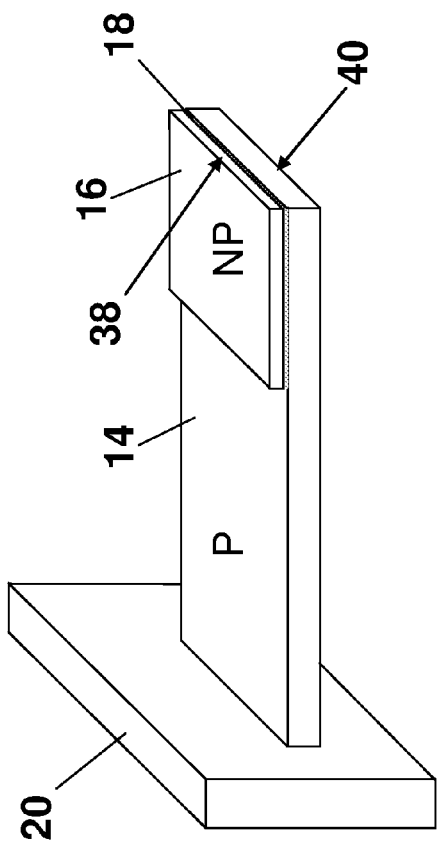
FIG. 5 is an illustration of an example configuration of a self-exciting, self-sensing piezoelectric cantilever sensor wherein the distal end of the piezoelectric layer is flush with the distal end of the non-piezoelectric layer.
Figure 6:
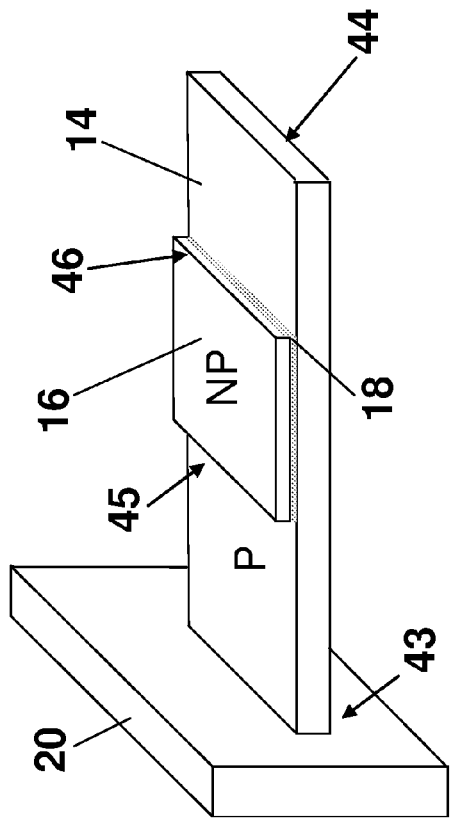
FIG. 6 is an illustration of an example configuration of a self-exciting, self-sensing piezoelectric cantilever sensor wherein the distal end of the piezoelectric layer extends beyond the distal end of the non-piezoelectric layer and the proximate end of the piezoelectric layer extends beyond the proximate end of the non-piezoelectric layer.

The PEMC sensor can be configured in accordance with a plurality of configurations, some of which are depicted in FIG. 5 and FIG. 6. It is to be understood however, that the configurations depicted herein do not represent all possible configurations, but rather a representative sample of configurations of the PEMC sensor. FIG. 5 is an illustration of an example configuration 36 of an unanchored PEMC sensor wherein the distal end 40 of the piezoelectric portion 14 is flush with the distal end 38 of the non-piezoelectric portion 16. The PEMC sensor 36 is termed "unanchored" because the non-piezoelectric portion 16 is not attached to the base portion 20. The piezoelectric portion 14 is coupled to the non-piezoelectric portion 16 via adhesive portion 18. The adhesive portion 18 is positioned between the overlapping portions of the piezoelectric portion 14 and the non-piezoelectric portion 16. The piezoelectric portion 14 is coupled to a base portion 20.

FIG. 6 is an illustration of an example configuration 42 of an unanchored PEMC sensor wherein the distal end 44 of the piezoelectric portion 14 extends beyond the distal end 46 of the non-piezoelectric portion 16 and the proximate end 43 of the piezoelectric portion 14 extends beyond the proximate end 45 of the non-piezoelectric portion 16. The piezoelectric portion 14 is coupled to the non-piezoelectric portion 16 via adhesive portion 18. The adhesive portion 18 is positioned between the overlapping portions of the piezoelectric portion 14 and the non-piezoelectric portion 16. The piezoelectric portion 14 is coupled to the base portion 20.

Figure 7:
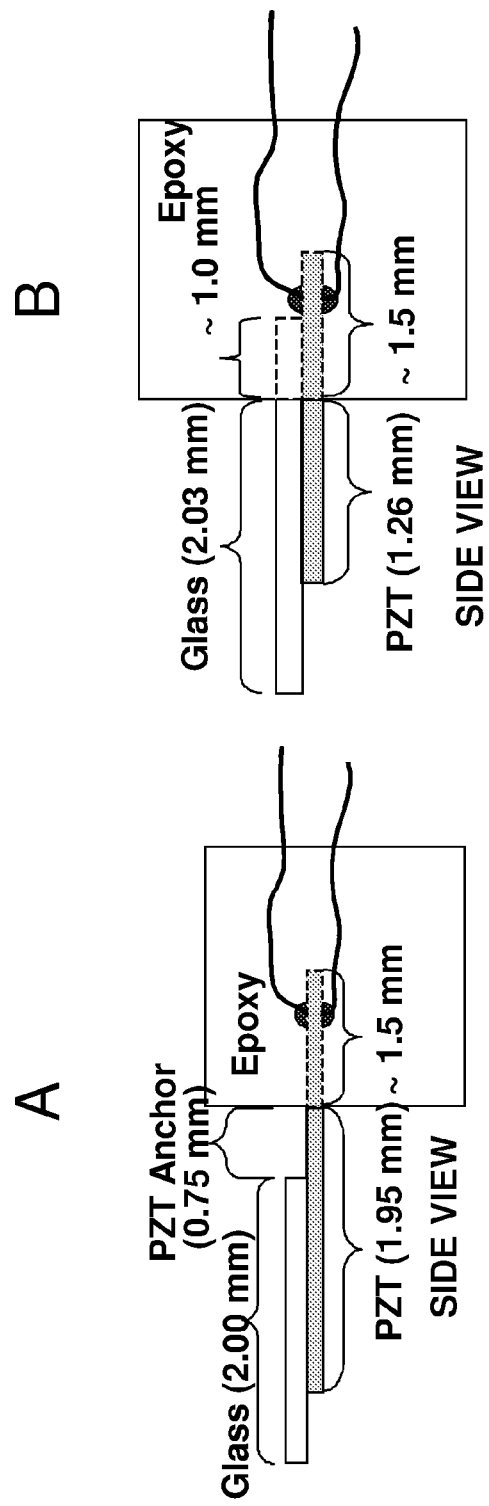
FIG. 7 is an illustration of cross sectional view of two example PEMC sensor configurations.

FIG. 7 is an illustration of cross sectional view of two example PEMC sensor configurations A and B. As depicted in configuration A, the non-piezoelectric portion is not in contact with the base. As depicted in configure B, the non-piezoelectric portion is in contact with the base.

Sensor Flow Cell

Figure 8:
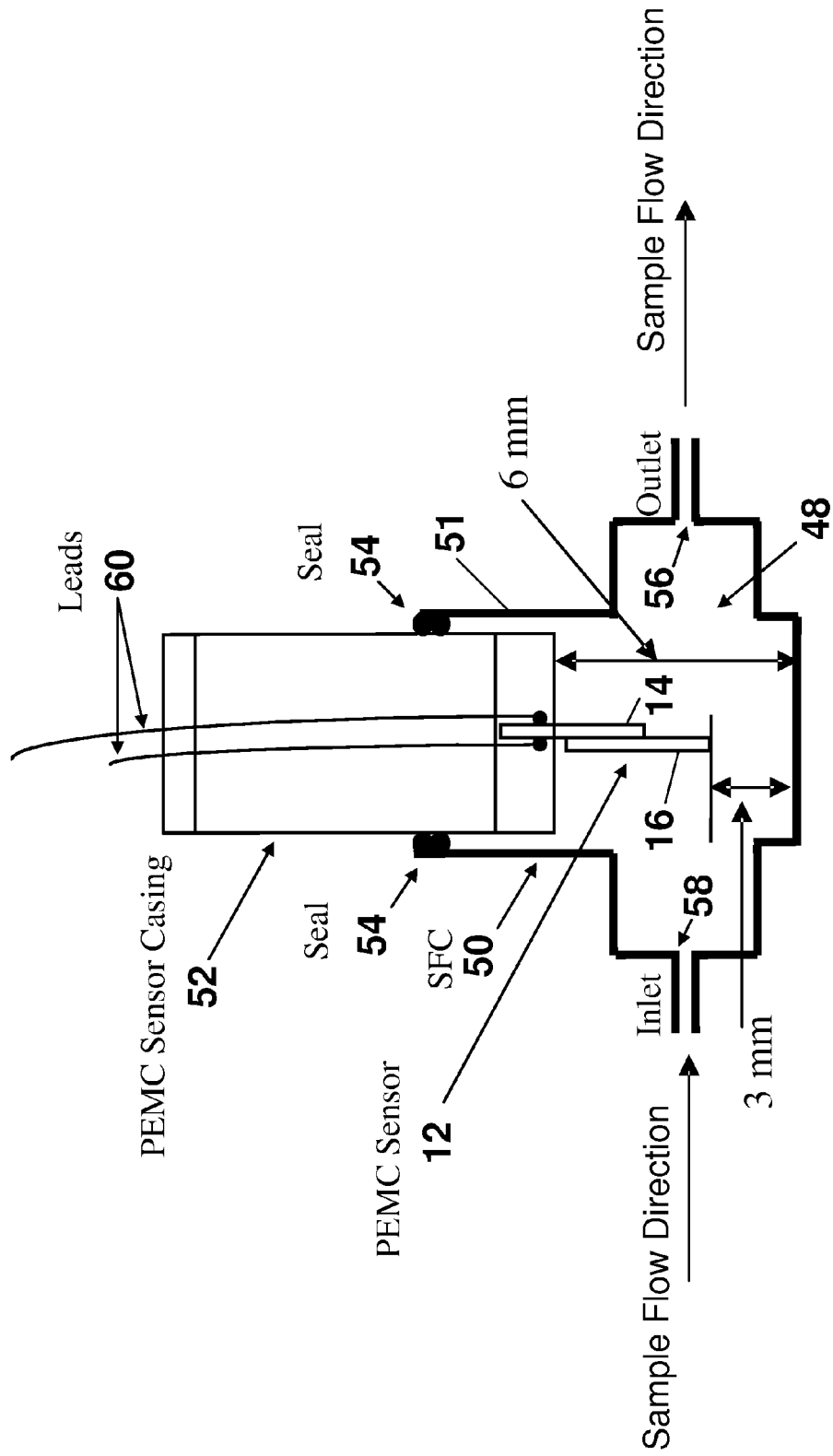
FIG. 8 is an illustration of a cross sectional view of an example sensor flow cell (SFC).

FIG. 8 is an illustration of a cross sectional view of an example sensor flow cell (SFC) 50. As depicted in FIG. 8, the PEMC sensor 12 is positioned in a reservoir portion 48 of the flow cell 50, wherein a medium (e.g., fluid: liquid or gas) is allowed to flow through the reservoir portion 48 via inlet aperture 58 and outlet aperture 56. In an example configuration, the PEMC sensor 12 is positioned in the reservoir portion 48 in the sample fluid flow from flow inlet aperture 58 to flow outlet aperture 56, by holding the PEMC sensor 12 in a sensor casing 52. The surfaces of the piezoelectric layer 14 of the PEMC sensor 12 are connected via leads 60 to a suitable measuring device (measuring device not shown in FIG. 8). The leads 60 are depicted as electrical conductors; however any appropriate leads can be utilized, such as inductive leads for example. Seal 54 (e.g., o-rings) or any suitable fitting can be provided to seal the flow cell 50 to the sensor casing 52.

Figure 9:
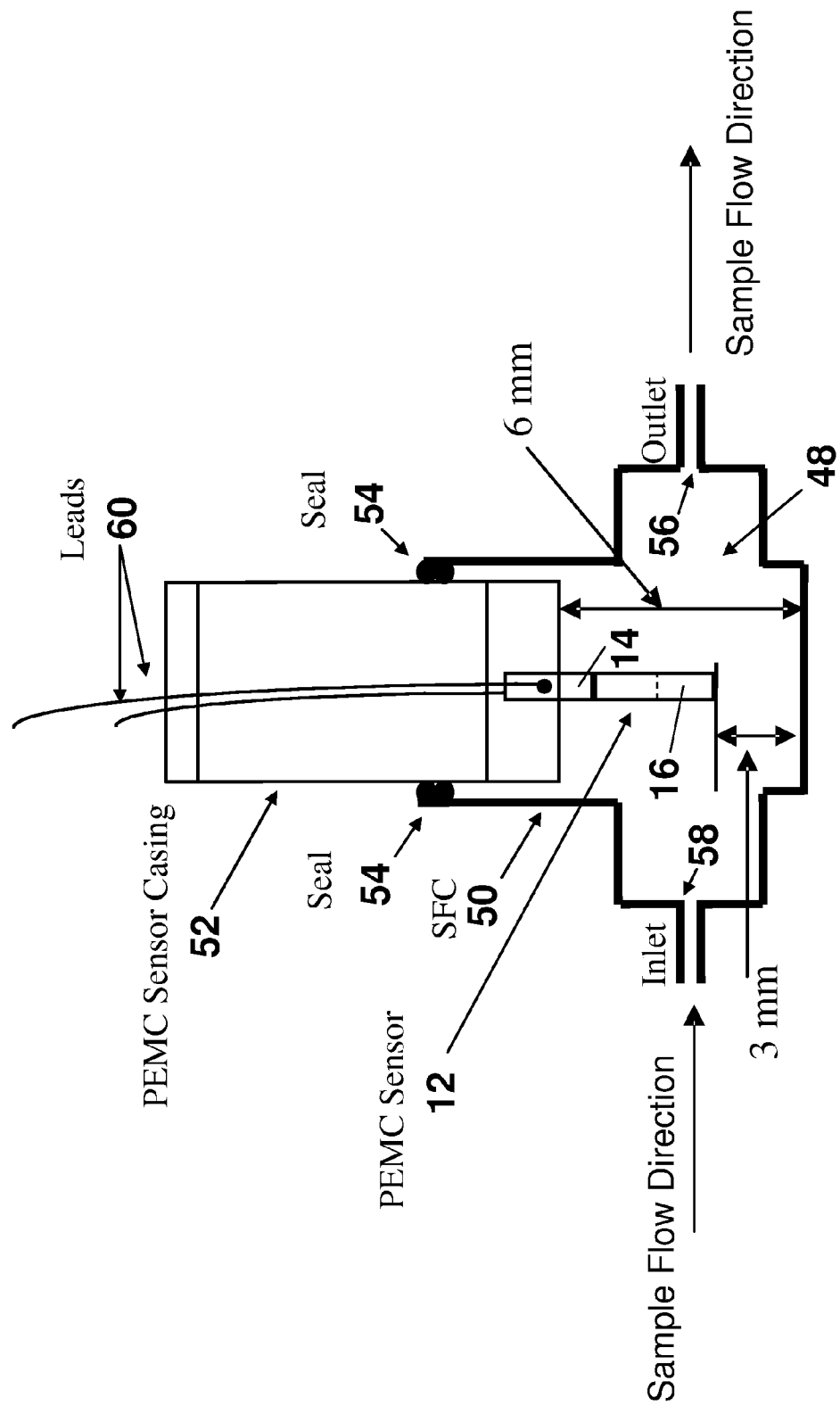
FIG. 9 is an illustration of a cross sectional view of an example SFC, wherein the PEMC sensor is rotated with respect to the PEMC sensor in FIG. 8.

As depicted in FIG. 8, the sensing surface(s) of the non-piezoelectric layer 16 is shown positioned perpendicular to the sample flow direction in the reservoir portion 48, directly between flow inlet aperture 58 and flow outlet aperture 56, allowing a significant spacing below and around the non-piezoelectric layer 16 for sample fluid flow past the sensing surface of the non-piezoelectric layer 16. This positioning of the PEMC sensor 12 however, is exemplary and not limited thereto. For example, as depicted in FIG. 9, sensing surface 16 is positioned parallel to the sample flow direction (e.g., rotating the sensor 12 as positioned in FIG. 8 by ninety degrees about a vertical, longitudinal, axis). Various configurations and flow directions are applicable. For example, the sample flow directions of can be reversed such that sample flows into outlet aperture 56 and out of inlet aperture 58. In an example configuration, the flow inlet aperture 58 and the flow outlet aperture 56 comprise the same internal diameter of 1.59 mm. Any appropriate dimensions for the flow cell 50 and PEMC sensor casing 52 can be utilized. In an example configuration, the PEMC sensor casing 52 has an internal diameter of 6.2 mm, the flow inlet aperture 58 and the flow outlet aperture 56 each have an internal diameter of $\frac{1}{16}$ of an inch and were located at substantially the same height in the flow cell 50, approximately 3 mm from the bottom of the flow cell 50. Flow inlet aperture 58 and flow outlet aperture 56 are positioned at a low point of the non-piezoelectric layer 16 to provide horizontal sample flow perpendicular to the sensing surface of the non-piezoelectric layer 16, as depicted in FIG. 8 and FIG. 9. Although the flow inlet aperture 58 and the flow outlet aperture 56 are positioned approximately 3 mm from the bottom of the flow cell 50, the positioning of the flow inlet aperture 58 and the flow outlet aperture 56 relative to the PEMC sensor 12 is not limited thereto. The flow inlet aperture 58 and the flow outlet aperture 56 can be positioned at any appropriate height relative to the PEMC sensor 12.

In operation, before starting the detection process, a binding agent for a target analyte is immobilized on the sensing surface of the non-piezoelectric layer 16. The PEMC sensor 12 is positioned in the flow cell 50, a medium (e.g., fluid:

liquid and/or gas) is run through the reservoir portion 48 via inlet aperture 58 and outlet aperture 56. As the medium flows through the reservoir portion 48, target analyte present in the medium binds to the binding agent on the non-piezoelectric layer 16 of the PEMC sensor 12. Causing the medium to flow through the reservoir portion 48, rather than allowing the PEMC sensor to sit in a static medium, results in improved detection performance. That is, as described in more detail below, more target analyte is accumulated on the sensing surface of the non-piezoelectric layer 16 when placed in flowing medium than when placed in static medium.

Figure 10:
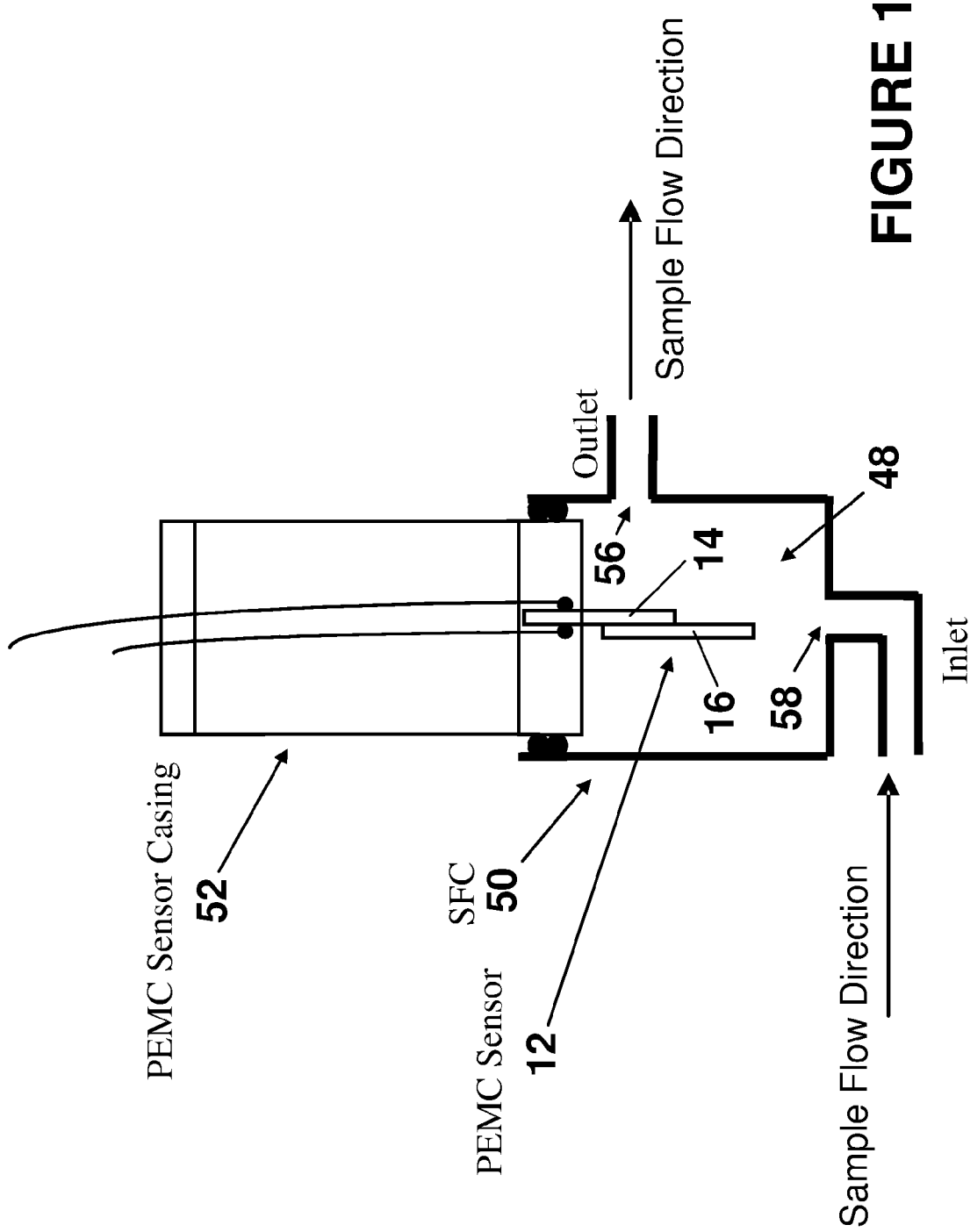
FIG. 10 is an illustration of a cross sectional view of another configuration of the example SFC.

FIG. 10 is an illustration of a cross sectional view of another configuration of the example sensor flow cell (SFC) 50, wherein the inlet aperture 58 is positioned at the bottom of the flow cell 50 and the outlet aperture 56 is positioned at the side of the flow cell 50. As depicted in FIG. 10, the PEMC sensor 12 is positioned in the reservoir portion 48 in the sample fluid flow from inlet aperture 58 to outlet aperture 56. The sample flow directions, dimensions, and relative positions of the PEMC sensor casing 52, the flow cell 50, the inlet aperture 58, and the outlet aperture 56, can comprise any appropriate dimension and position. For example, the sample flow directions of can be reversed such that sample fluid flows into outlet aperture 56 and out of inlet aperture 58. In an example configuration, the flow inlet aperture 58 and the flow outlet aperture 56 comprise the same internal diameter of 1.59 mm. In another example configuration, the flow inlet aperture 58 and the flow outlet aperture 56 comprise the same internal diameter of 1.4 mm.

As depicted in FIG. 10, the sensing surface of the non-piezoelectric layer 16 of the PEMC sensor 12 is positioned parallel to the inlet flow direction, directly above inlet aperture 58, allowing a spacing below and around the non-piezoelectric layer 16 for sample fluid flow past the sensing surface of the non-piezoelectric layer 16 to flow outlet aperture 56. A characteristic of the flow cell configuration of the flow cell depicted in FIG. 10 is that the resonance frequency of the PEMC sensor 12 does not fluctuate significantly as a function of flow rate of the medium. Another characteristic of the configuration depicted in FIG. 10 is that a stepwise increase in resonance frequency occurs as sample flow of the medium is initiated, until a constant resonance frequency is achieved.

Figure 11:
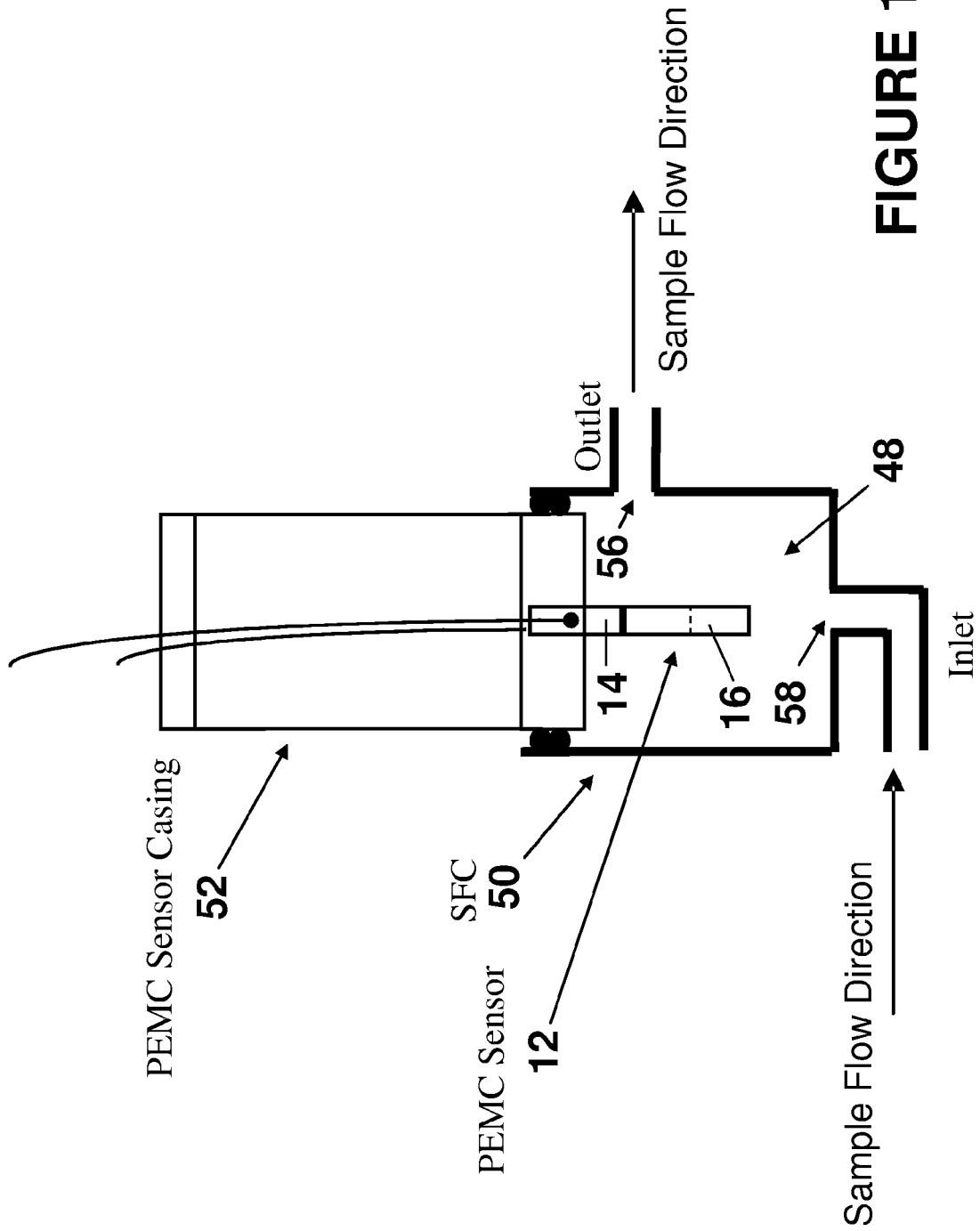
FIG. 11 is an illustration of a cross sectional view of an example SFC, wherein the PEMC sensor is rotated with respect to the PEMC sensor in FIG. 10.

The positioning of the PEMC sensor 12 is exemplary and not limited thereto. For example, as depicted in FIG. 11, the PEMC sensor 12 rotated by ninety degrees about a vertical, longitudinal, axis. Further, as with each example configuration depicted herein, multiple variations and flow directions are applicable. For example, the sample flow directions of the medium can be reversed such that medium flows into outlet aperture 56 and out of inlet aperture 58.

In an example configuration of the flow cell type depicted in FIG. 10 and FIG. 11, the lowermost tip of the PEMC sensor 12 (e.g., non-piezoelectric layer 16) is positioned at least three millimeters from the inlet aperture 58. Also in this example configuration, the outlet aperture 56 is located directly in line with the thickest portion of the PEMC sensor 12 where the piezoelectric layer 14 and non-piezoelectric layer 16 are bonded together in order to minimize flow disturbances in the vicinity of the PEMC sensor 12.

The velocity of the medium in the flow cell 50 can be oriented approximately parallel to the longitudinal axis of the PEMC sensor 12 to increase contact between medium flow and the PEMC sensor 12. In an example embodiment, the velocity of the medium flow in the flow cell 50 is selected to be less than 0.1 cm/second to obtain improved sensitivity performance over a static medium. In another example embodiment, the inner diameter of the inlet aperture 48 is a large as 3 mm to provide stable resonance peaks. In an example configuration, the inner diameter of the inlet aperture 48 is 1.6 mm.

In an example embodiment, a flow cell and a PEMC sensor are separate and detachable. Thus, a flow cell can be fabricated allowing for the insertion, attachment, or the like, of a PEMC sensor, or PEMC sensors. A PEMC sensor and a flow cell can be attached via any appropriate means, such as threaded insertion, snap and lock insertion, or a combination thereof, for example. In another example embodiment, the flow cell and the PEMC sensor, or PEMC sensors, is a single integrated entity. Thus, in an example embodiment, the integrated flow cell and PEMC sensor(s) are be fabricated as a single unit. The unit can be reusable and/or disposable.

Figure 12:
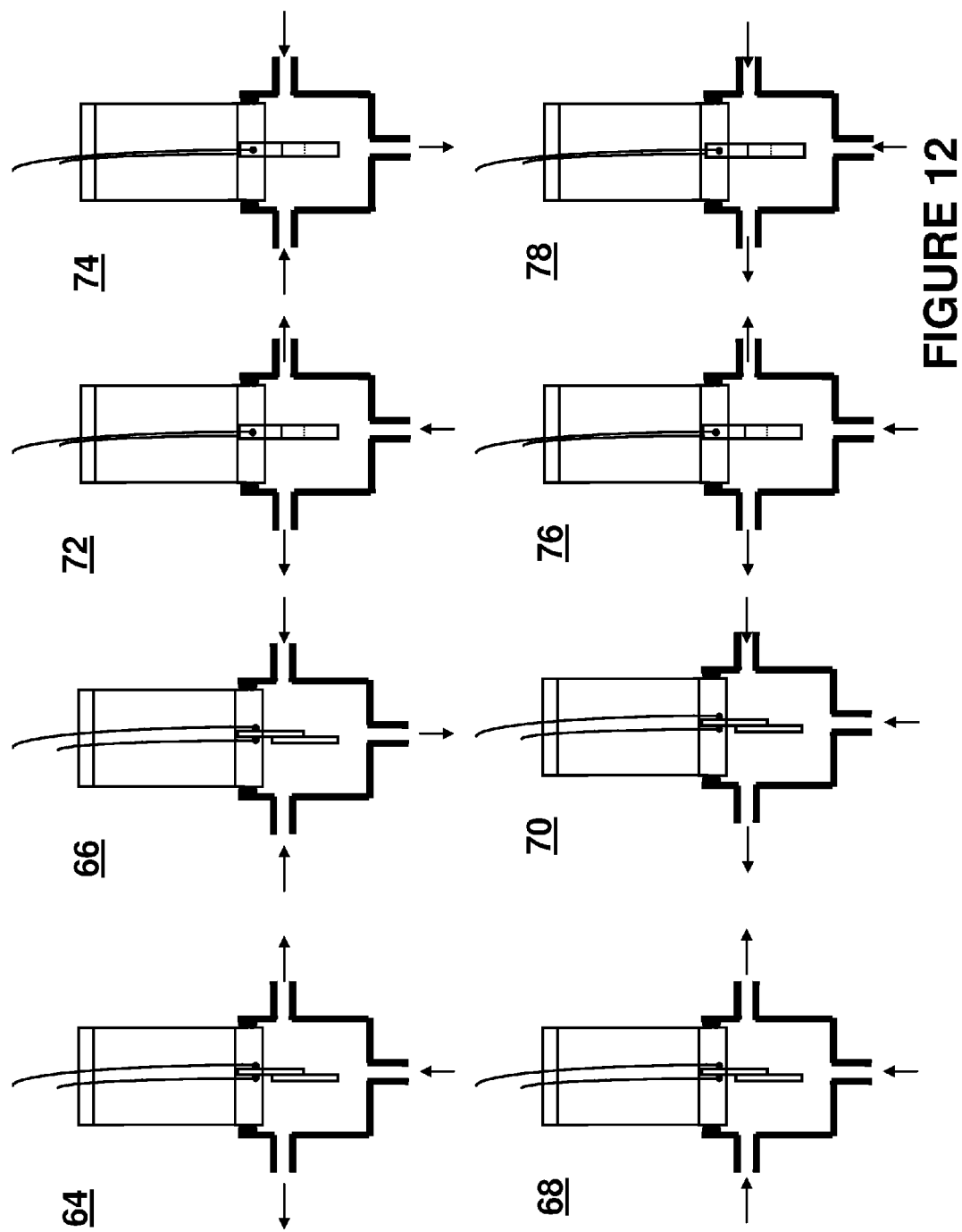
FIG. 12 is an illustration of a cross sectional view of eight example flow cell configurations.
Figure 13:
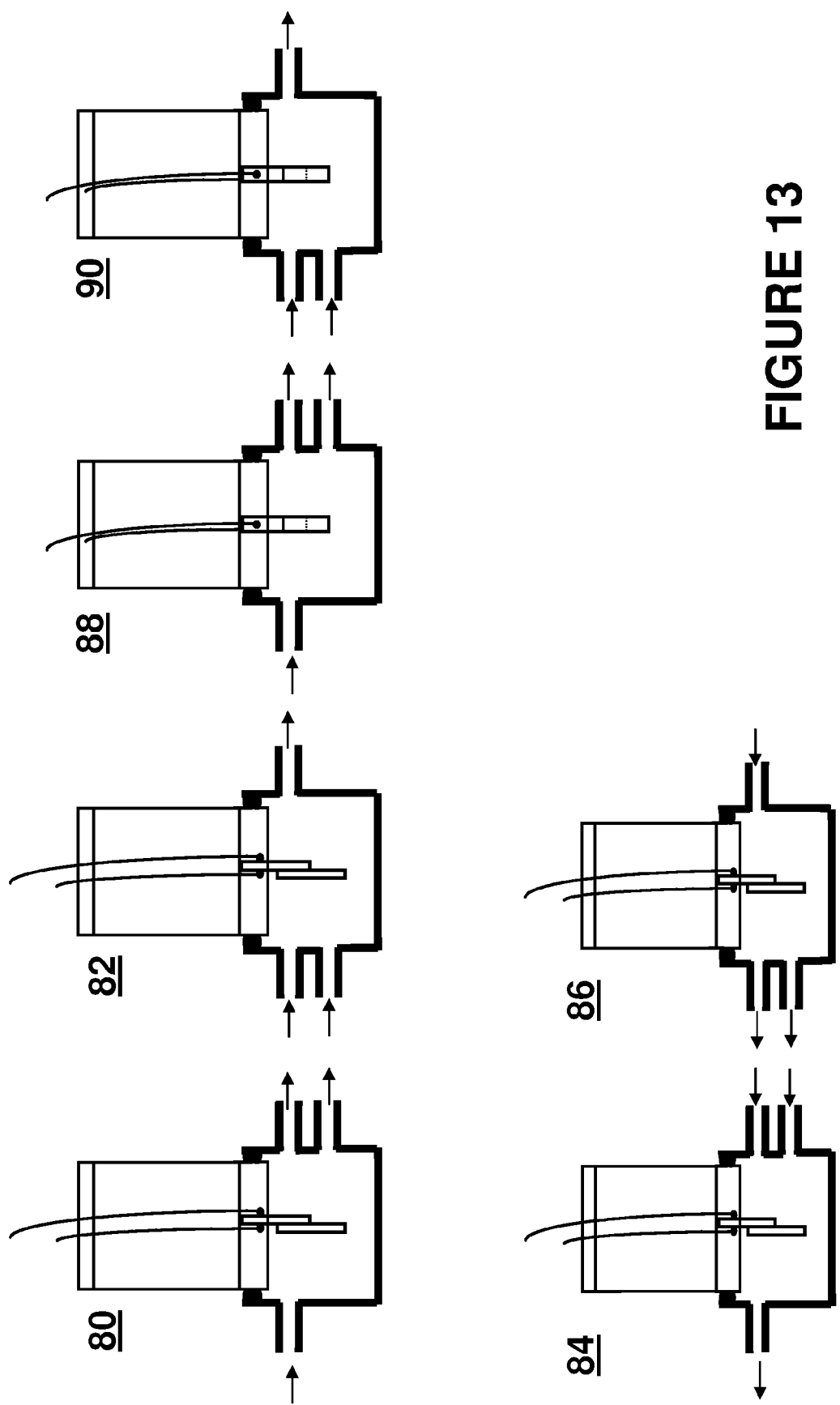
FIG. 13 is an illustration of a cross sectional view of six example flow cell configurations.

Flow cells for use with the PEMC sensor can be configured in numerous configurations. Some example configurations are shown in FIG. 12, FIG. 13, and FIG. 14. It is to be understood however, that flow cell configurations are not limited to the configurations depicted herein.

FIG. 12 is an illustration of a cross sectional view of eight example flow cell configurations. Configuration 64 depicts a flow cell comprising three apertures. Two outlet apertures are positioned on the sides of the flow cell and an inlet aperture is positioned on the bottom of the flow cell. Configuration 66 depicts a flow cell comprising three apertures. Two inlet apertures are positioned on the sides of the flow cell and an outlet aperture is positioned on the bottom of the flow cell. Configuration 68 depicts a flow cell comprising three apertures. One inlet aperture is positioned on the side of the flow cell and another inlet aperture is positioned on the bottom of the flow cell. One outlet aperture is positioned on the sides of the flow cell. Configuration 70 depicts a flow cell comprising three apertures. One inlet aperture is positioned on the side of the flow cell and another inlet aperture is positioned on the bottom of the flow cell. One outlet aperture is positioned on the sides of the flow cell. Configurations 72, 74, 76, and 78, are similar to configurations 64, 66, 68, and 70, respectively; however the PEMC sensor is rotated about a vertical, longitudinal, axis. As depicted in configurations 72, 74, 76, and 78, the PEMC sensor is rotated approximately 90 degrees about its vertical, longitudinal, axis with respect to the orientation of the PEMC sensor depicted in configurations 64, 66, 68, and 70, respectively, but is not limited thereto. As applicable to all flow cell configurations, the PEMC sensor can be rotated by any appropriate number of degrees about its vertical, longitudinal, axis. The configurations depicted in FIG. 12 can be varied to allow the location of inlet and outlet apertures to vary and to allow the orientation of the PEMC sensor about its vertical, longitudinal, axis to vary. For example, the apertures located on the sides of the flow cell can be of different heights from the bottom of the flow cell. Thus, referring to configuration 64 as an example, the aperture on the left of the flow cell can remain at it depicted location and the aperture on the right of the flow cell can be positioned lower, closer to the bottom of the flow cell. Additionally, the location of the aperture at the bottom of the flow cell can be varied (e.g., moved to the left or right).

FIG. 13 is an illustration of a cross sectional view of six example flow cell configurations. Configuration 80 depicts a flow cell comprising three apertures. Two outlet apertures are positioned on the side of the flow cell and an inlet aperture is positioned on the side of the flow cell. Configuration 82 depicts a flow cell comprising three apertures. Two inlet apertures are positioned on the side of the flow cell and an outlet aperture is positioned on the side of the flow cell. Configuration 84 depicts a flow cell comprising three apertures. Two inlet apertures are positioned on the side of the flow cell and an outlet aperture is positioned on the side of the flow cell. As depicted in configuration 84, the PEMC sensor has been rotated 180 degrees about its vertical, longitudinal, axis with respect to the orientation of the PEMC sensor as depicted in configuration 82. Configuration 86 depicts a flow cell comprising three apertures. One inlet aperture is positioned on the side of the flow cell and two outlet apertures are positioned on the side of the flow cell. As depicted in configuration 86, the PEMC sensor has been rotated 180 degrees about its vertical, longitudinal, axis with respect to the orientation of the PEMC sensor as depicted in configuration 80. Configurations 88 and 90 are similar to configurations 80 and 82, respectively; however the PEMC sensor is rotated about a vertical, longitudinal, axis. As depicted in configurations 88 and 90, the PEMC sensor is rotated approximately 90 degrees about its vertical, longitudinal, axis with respect to the orientation of the PEMC sensor as depicted in configuration 80 and 82, respectively, but is not limited thereto. As applicable to all flow cell configurations, the PEMC sensor can be rotated by any appropriate number of degrees about its vertical, longitudinal, axis. It is to be understood that the depicted flow cell configurations are exemplary and not limited thereto. For example, the flow cell can comprise a plurality of apertures on the side of the flow cell and a plurality of apertures on the bottom of the flow cell.

FIG. 14 is an illustration of a cross sectional view of example flow cell configurations comprising multiple PEMC sensors. A flow cell configured for a PEMC sensor can comprise a single PEMC sensor or multiple PEMC sensors. Each of multiple PEMC sensors can be configured to detect the same target analyte, to detect different respective target analytes, to function as a control sensor, or a combination thereof. In an example embodiment, a control sensor, or multiple control sensors, is immobilized (not treated to attract a target material) for reducing noise, for calibration, or the like.

Configuration 89 depicts a flow cell comprising two PEMC sensors. Configuration 91 depicts a flow cell comprising more than two PEMC sensors. PEMC sensors can be positioned at any appropriate location. Configuration 93 depicts a flow cell comprising multiple PEMC sensors positioned at opposite ends of the flow cell. Configuration 95 depicts a flow cell comprising multiple PEMC sensors positioned at an end and on a side the flow cell. Configuration 97 depicts another flow cell comprising multiple PEMC sensors positioned at an end and on a side the flow cell.

Generally, flow cells configured for a PEMC sensor that exhibit substantially constant pressure fields, give rise to low noise in measurement and provide stable resonance peaks. The flow cell may show sensitivity to flow rate, if pressure gradients exist in the flow cell therein. Flow cells configured for a PEMC sensor allow detection of analytes using a PEMC sensor in large sample volumes. When a sample contains target analytes such as pathogens (e.g.: *E. coli* 0157:H7, *Bacillus anthracis* spores, Group A *Streptococcus pyrogens*), typically such analytes are present at low concentrations (a few hundred/mL) in large sample volumes. Used conventionally in a stagnant environment, a millimeter-sized sensor can not reliably sample a large volume of sample. Thus contacting the sample with the sensor can be accomplished by flow of the sample relative to the PEMC sensor. In a stagnant sample the analyte pathogens settle due to density differences and cause poor sensor response or even give false negative results. The herein described flow cells configured for a PEMC sensor minimize settling due to density variations and do not compromise the sensitivity of PEMC.

Contacting the sample medium comprising analyte with the PEMC sensor under flow conditions results in a higher binding rate of analyte as compared to contacting the PEMC sensor with static medium. Since the PEMC sensor has a fixed binding area, the available sites decrease as it is exposed to analyte. Flow improves transport of analyte to the PEMC sensor surface thereby increasing the probability of analyte binding to the fixed binding area of the PEMC sensor and thereby facilitating detection of lower concentrations of analyte in the sample volume.

Methods of detecting analytes in fluid media utilizing a flow cell configured for a PEMC sensor include exposing a PEMC sensor to the media under flow conditions in a flow cell. Optionally analyte can be removed from the PEMC sensor and the sensor can be reused to detect analyte in the media. This can be repeated several times depending on the nature of the binding agent and the analyte. This allows reuse of the flow cell and PEMC sensor several times without having to replace the PEMC sensor. The analyte may be removed from the PEMC sensor surface by any suitable manner for breaking the covalent bonds between the binding agent and the analyte (e.g., rinse, vibration, fluid flow).

Flow cells configured for PEMC sensors as described herein minimize fluctuations in PEMC sensor response due to media flow, e.g., as little as 20 Hz in the 0.0 to 20 mL/min flow range. Additionally, the sensitivity of the PEMC sensor is not compromised and the PEMC sensor response is higher under flow conditions due to superior binding of the target analyte to the sensor surface. Also, the herein described flow cells configured for PEMC sensors offer a mass change sensitivity of about 10 ag/Hz or better under liquid-submerged conditions, and are about 1000 times more sensitive than quartz crystal microbalance and about one billion fold times more sensitive than analytical instruments.

Experiments

Experiments were conducted using various embodiments of the herein described flow cells configured for PEMC sensors. Detection of pathogens and proteins at concentrations as low as a few hundred per mL and pg/mL, respectively were demonstrated by measuring directly in liquid using a PEMC sensor immobilized with antibodies specific to a target analyte. The PEMC sensor also detected target analytes without false positives or negatives even when contaminating entities were present in the medium. For example, *E coli* 0157:H7 was successfully detected in ground beef without enrichment at less than 10 pathogen/mL. Staphlococcal enterotoxin B was detected at 2.5 fg/mL in buffers, milk and in apple juice under fully submerged conditions. Ovarian cancer antigen, CA-125 was detected in human serum at 1.25 ag/mL. The samples do not have to be specially prepared, concentrated or enriched for detection. Detection can be conducted directly in raw samples in liquid form (or gas) or in samples that can be diluted into liquid form with a suitable, conventional diluent.

Concentrated sulfuric acid ($H_2SO_4$), methanol, hydrochloric acid, sodium hydroxide, 3-aminopropyl-triethoxysilane (APTES), 1-ethyl-3-(3-dimethylaminopropyl)-carbodiimide (EDC), sulfo-N-hydroxysuccinimide (sulfo-NHS), phosphate buffered saline (PBS: pH 7.4), hydroxylamine, and 2-mercaptoethanol were all purchased from Sigma-Aldrich (Allentown, Pa.). Deionized water used was from a Milli-Q plus ultra-pure water system (17.2 MΩcm).

Two flow cells configurations as depicted in FIG. 8 and FIG. 10 were used to show results at high flow rates. For purposes of describing experiments, the flow cell configuration depicted is FIG. 8 is herein referred to as Sample Flow Cell 1 (SFC-1) and the slow cell configuration depicted in FIG. 10 is referred to as Sample Flow Cell 2 (SFC-2). The flow cells were constructed of Plexiglas® and dimensional details are given in FIG. 8. The central contacting chamber 51 was cylindrical in shape and was 6.0 mm in diameter. Once a PEMC sensor was installed, the hold up volume was 500 μL and 300 μL in SFC-1 and SFC-2, respectively. The hold up volume is the volume occupied by the fluid in the SFC. The hold up volume is equal to the volume of the SFC minus the volume occupied by the PEMC sensor. The difference between the two flow cells SFC-1 AND SFC-2 is the position of the inlet and the outlet apertures. In SFC-1 both the inlet aperture and outlet aperture are positioned horizontally at the lowest point on the sides of the flow cell, as depicted in FIG. 8. In SFC-2, the inlet aperture and outlet aperture are located at the bottom and on the side of the flow cell, respectively, as depicted in FIG. 10. The outlet aperture 56 of SFC-2 (FIG. 10) has an inner diameter of 1.59 mm and was located 4 mm above the inlet aperture 58, which also had an inner diameter of 1.59. Constant temperature water (35±0.1° C.) was circulated (17 mL/min) through a shell (not shown in the figures) surrounding the flow cell. The shell (4 mm wide) was 2 mm from the cell inner surface. At steady state, the temperature within the flow cell varied by ±0.2° C. in the sample flow range of 1 to 17 mL/min.

PEMC sensors were manually fabricated as a composite structure of two layers: a 127 mm thick PZT (piezoelectric ceramic lead zirconate titanate) single sheet (Piezo Systems Inc., Cambridge, Mass.) and a 160 μm thick borosilicate cover glass slip (Fisher Scientific). Both the PZT and the glass cover slip were 5×1 mm (length×width). The composite cantilever was fabricated by bonding the PZT to the cantilever glass base with a non-conductive adhesive such that a 2 mm length of the glass protruded to provide surface for antibody immobilization and antigen detection. The top and bottom surface of the 2 mm PZT layer was soldered to a 30 gauge copper wire connected to BNC couplers. The soldered end was encapsulated into a glass tube (6 mm OD) with a non-conductive epoxy such that 1.0 mm of the bonded PZT layer protruded out of the encapsulated glass tube. The exposed PZT layer (1 mm) was coated with a thin layer of polyurethane (about 20 μm) for protection in submerged liquid conditions.

The cantilever sensing glass surface was cleaned sequentially with methanol-hydrochloric acid solution (1:1 volume per volume, v/v), concentrated sulfuric acid, hot sodium hydroxide, and finally boiling water. After cleaning, the glass surface was silanylated with 0.4% 3-aminopropyl-triethoxysilane (APTES; Sigma-Aldrich) in deionized water at pH 3.0 (adjusted by hydrochloric acid, 0.1 N) and 75° C. for 2 hours. The APTES functionalized sensor was dried in an oven (Isotemp, model 280A, Fisher Scientific, PA) overnight at 80° C.

Antibody to *Bacillus anthracis* spores (anti-BA produced in rabbit and affinity purified) and antibody to Bovine Serum Albumin (anti-BSA: Sigma-Aldrich) were prepared in PBS of concentration 10 μg/mL. 4 mL of the antibody solution was activated with 1.6 mg 1-ethyl-3-(3-dimethylaminopropyl)-carbodiimide (EDC, final concentration about 2 mM) and 4.4 mg sulfo-N-hydroxysuccinimide (sulfo-NHS, final concentration about 5 mM) at room temperature for 30 minutes. Then 2.0 μL of 2-mercaptoethanol (final concentration 20 mM) was added to quench the EDC reaction for 15 minutes.

Figure 15:
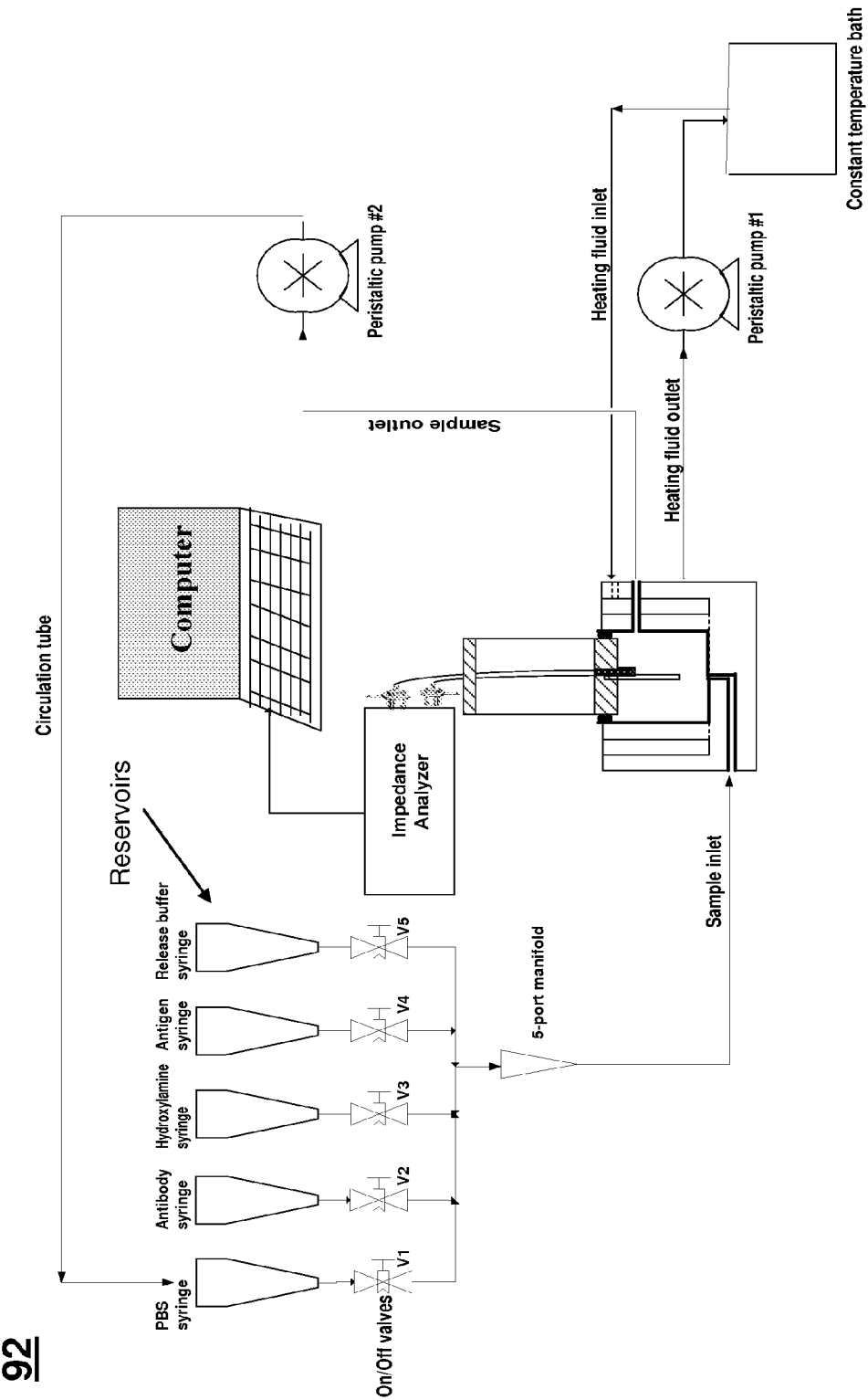
FIG. 15 is an illustration of an example system comprising a flow cell configured for a PEMC sensor.

The experimental system 92 comprised fluid reservoirs, peristaltic pumps, and a sensor flow cell (SFC-2) as shown in FIG. 15. The system 92 comprised five fluid reservoirs: for PBS buffer pH 7.4, activated antibody solution, 10 mM hydroxylamine solution, antigen sample, and release buffer (PBS/HCl; pH 2.0). The liquid reservoirs were connected to the flow cell via a five entrance port manifold, and the inflow enters the SFC through the bottom. The outlet of the flow cell is connected to a peristaltic pump, which controls the flow of the desired fluid into and out of the SFC. The APTES functionalized PEMC sensor was installed vertically into the cell containing PBS and was secured by two O-rings. The cantilever electrodes were connected to an impedance analyzer (Agilent, HP 4192A) interfaced to a data acquisition PC with LabVIEW application for obtaining impedance and phase angle measurements in the frequency range of 1 to 200 kHz with an excitation voltage of 100 mV. The constant temperature bath was set at 35±0.1° C. in order to maintain the cell content at 25° C. The fluidic system was first primed with PBS to remove any air bubbles. Valves located at the bottom of each fluid reservoir enabled selection of fluid for introduction into the flow cell or for circulation. Switching the outlet line from the peristaltic pump into the desired fluid reservoirs enabled total recirculation. All valves were manipulated manually. All detection experiments were carried out at a flow rate of 1 mL/min.

An experiment was initiated by circulating PBS through the flow cell until the cantilever's resonance frequency reached a steady value, which was usually achieved in 10 minutes. Upon stabilization, the flow was switched to the next reservoir inline and the outlet from the peristaltic pump was directed back into the active reservoir. The time for each step during a detection experiment was varied: approximately 2 hours for antibody, 5 minutes for hydroxylamine and PBS, 1 hour for antigen sensing, and 1 hour for the antigen release.

The effect of flow rate on the measured resonance frequency of the PEMC sensors was determined by circulating deionized water through the cell at various flow rates. For each of the eleven flow rates investigated the measured resonance frequency was monitored for at least 15 minutes. The experiment was carried out at 25±0.1° C.

After the APTES functionalized sensor was installed in the SFC containing PBS the resonance frequency of the fundamental mode was monitored until it stabilized. Then, the activated antibody solution was flowed into the cell (by opening valve V2) after which the flow was stopped to allow antibody immobilization under stagnant conditions for 3 hours at 25±0.1° C. Hydroxylamine was then flowed through the cell (by opening V3), and then PBS (by opening valve V1 and closing V3) to rinse out the lines. Upon completion of the rinsing step, the antigen solution was introduced into the sensor flow cell by opening V4 and closing V1. After the antigen attachment was concluded V4 was closed, and the cell was rinsed with PBS (by opening V1) followed by flowing the release buffer (open V5 and close V1).

The flow patterns through the sensor flow cell were investigated by modeling the flow using finite element modeling platform, FEMLAB®. The two-dimensional Navier Strokes equation ($\rho=1000$ kg/m$^3$ and $\mu=0.001$ Pa·s) was solved in conjunction with continuity equation for various inlet flow rates (1 to 17 mL/min). The dimensions of the sensor flow cell used in the model were identical in shape and dimension to the actual ones used in the experiments within ±0.05 mm.

For the PEMC sensor investigated, the fundamental and second mode resonance frequencies were at 23±1 kHz and 91±2 kHz in air, respectively. Several repeat experiments showed that these resonance frequencies are stable within ±10 Hz in any one particular experiment. In this experiment, the fundamental mode was used for detection because the peak was very stable and remained sharp under various flow rates. Each experiment was repeated at least twice and the data shown are typical of the results obtained. The sharpness of the peak is characterized by its quality factor (Q-factor). Typical Q-factor values ranged from 30 to 100, and do not deteriorate significantly upon water immersion. The Q-factor of the fundamental mode in air was 50, and in PBS it was 42. In this experiment, it was observed that the PEMC sensor performance did not deteriorate at flow rates as high as 17 mL/min, which is approximately 200-fold higher than known cantilevers sensors.

Figure 16:
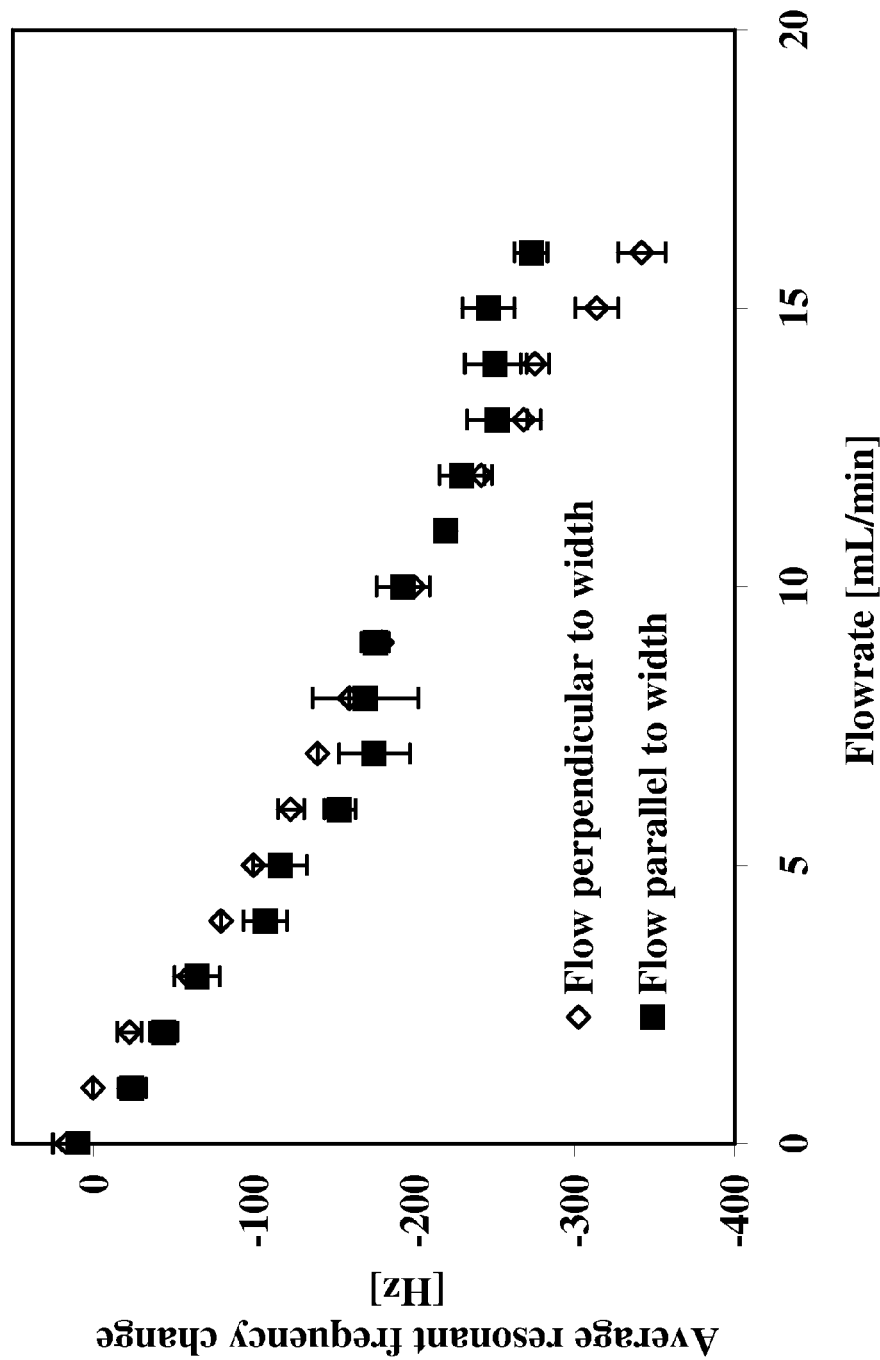
FIG. 16 a graph illustrating the response of the PEMC sensor to flow rate changes.

In FIG. 16 the response of the PEMC sensor to flow rate changes is presented. In FIG. 16, a flow sensitivity study is shown that was conducted in SFC-1 with the sensor in two different configurations; namely, the width of the sensor (1 mm) was positioned parallel or perpendicular to the inflow. The flow rate was systematically varied from 1 to 17 mL/min in steps of 1 mL/min. The resonance frequency decreased monotonically, and the parallel or perpendicular positioning of the PEMC sensor did not appear to have a significant effect on the direction or magnitude of change in resonance frequency. The resonance frequency decreased linearly at a rate of 22 Hz/mL/min and appeared to decrease further beyond 17 mL/min. When the sensor was placed parallel to the inflow, the decrease in resonance frequency with flow rate was linear up to 10 mL/min and further flow rate increases resulted in small changes in resonance frequency. Observed in the graph of FIG. 16, is that the fluctuation of resonance frequency at any particular flow rate was small, and was in the range of 8 to 15 Hz over the entire range of flow rates investigated.

Figure 17:
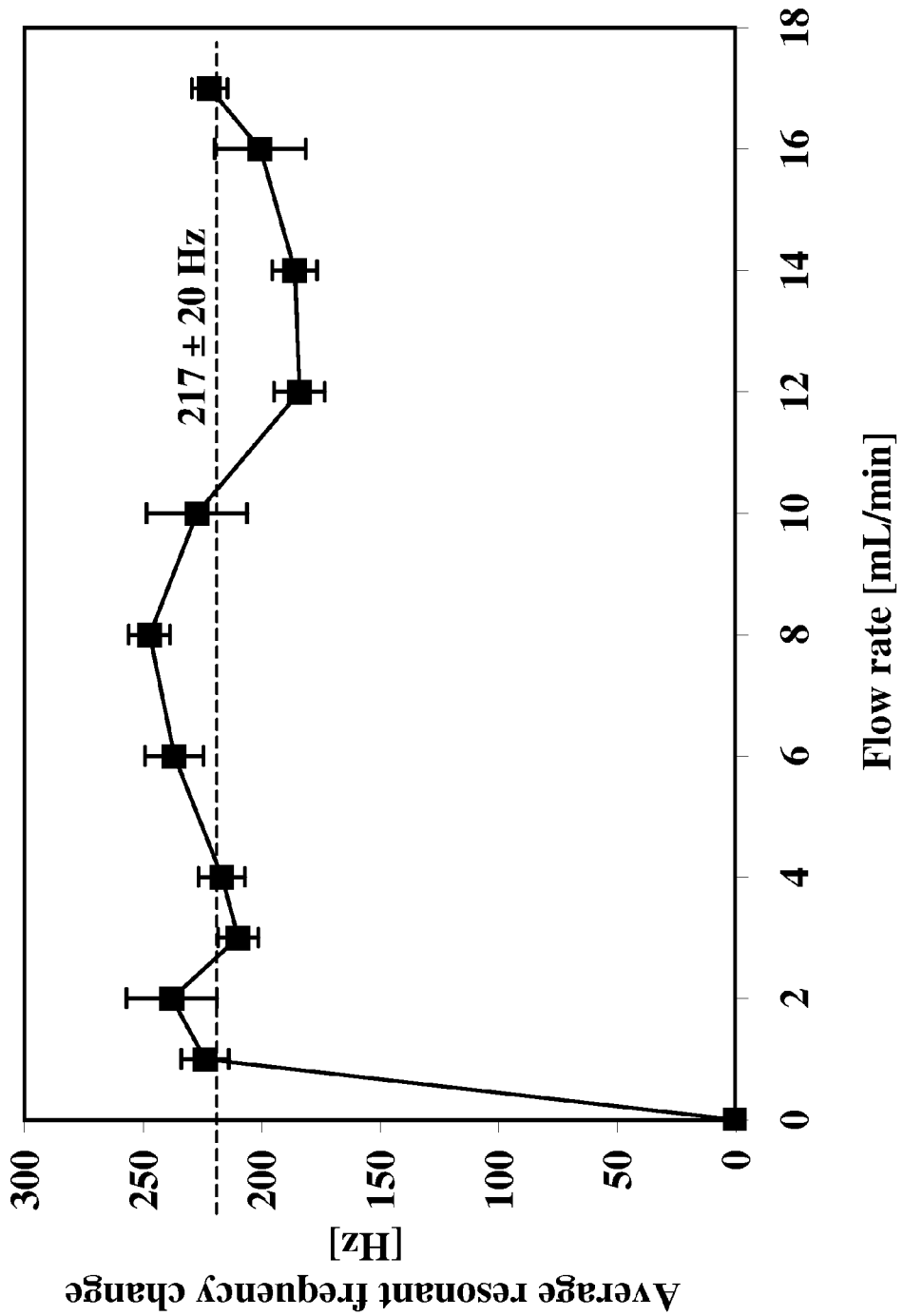
FIG. 17 is a graph depicting the average resonance frequency of a flow cell having inflow introduced from the bottom of the flow cell.

FIG. 17 is a graph depicting the results of testing the SFC-2 geometry with the inflow introduced from the bottom of the flow cell. As the flow for SFC-2 was initiated the resonance frequency increased initially in a step-like manner and then fluctuated around an average resonance frequency at each of the flow rates investigated in the range of 1 to 17 mL/min. At each flow rate, the flow was kept constant for 20 minutes and the average resonance frequency value and the corresponding standard deviation during the 20 minute time period are presented in FIG. 17. The maximum and minimum variations at any particular flow rate were +7 and ±20 Hz, respectively. This is slightly higher than the maximum and minimum variations found under stagnant conditions, ±5 Hz; adequate for sensing. Over the entire range of flow rate investigated, 1 to 17 mL/min, the mean resonance frequency change was 217 Hz with a standard deviation of ±20 Hz. These repeatable variations appear to be characteristics of the flow geometry of SFC-2.

Figure 18:
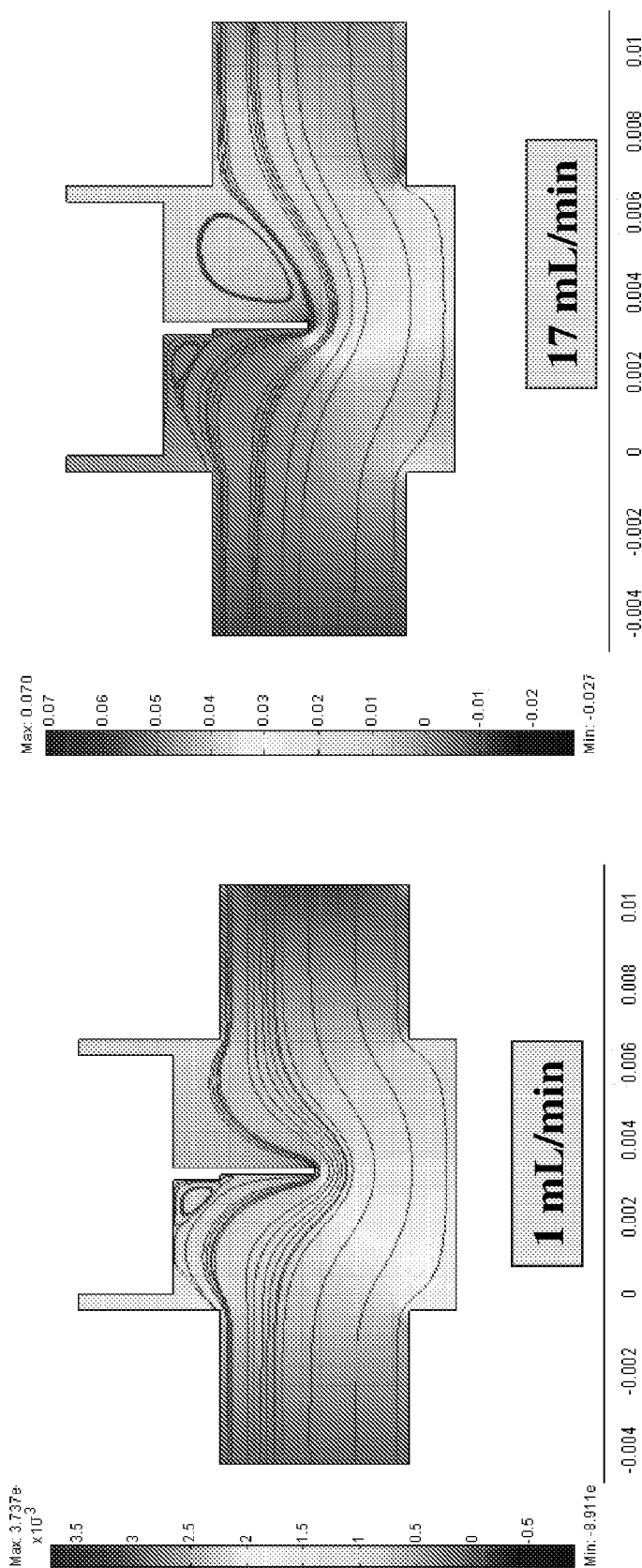
FIG. 18 is a graph illustrating a pressure map and velocity field in a flow cell at the various flow rates.

Because the initial increase in resonance frequency upon initiation of flow in the SFC-2 can be due to a pressure change in the cell, pressure maps and velocity profiles were obtained in order to compare sensor interaction characteristics. The pressure map and velocity field in the flow cells at the various flow rates were investigated, and the results for 1 and 17 mL/min are presented in FIG. 18. The plots in FIG. 18 illustrate surface plots 94 and 96 of pressure and the streamline of the velocity field for SFC-1, wherein the sensor is positioned with its width (1 mm) perpendicular to inflow (as depicted in FIG. 8), for flow rates of 1 mL/min and 17 mL/min, respectively. Even at a low flow rate (1 mL/min) the flow map showed a small re-circulation region adjacent to the sensor on the inlet side. As the flow rate was increased to 17 mL/min (plot 96) the re-circulating domain increased progressively on the opposite side of the sensor.

Figure 19:
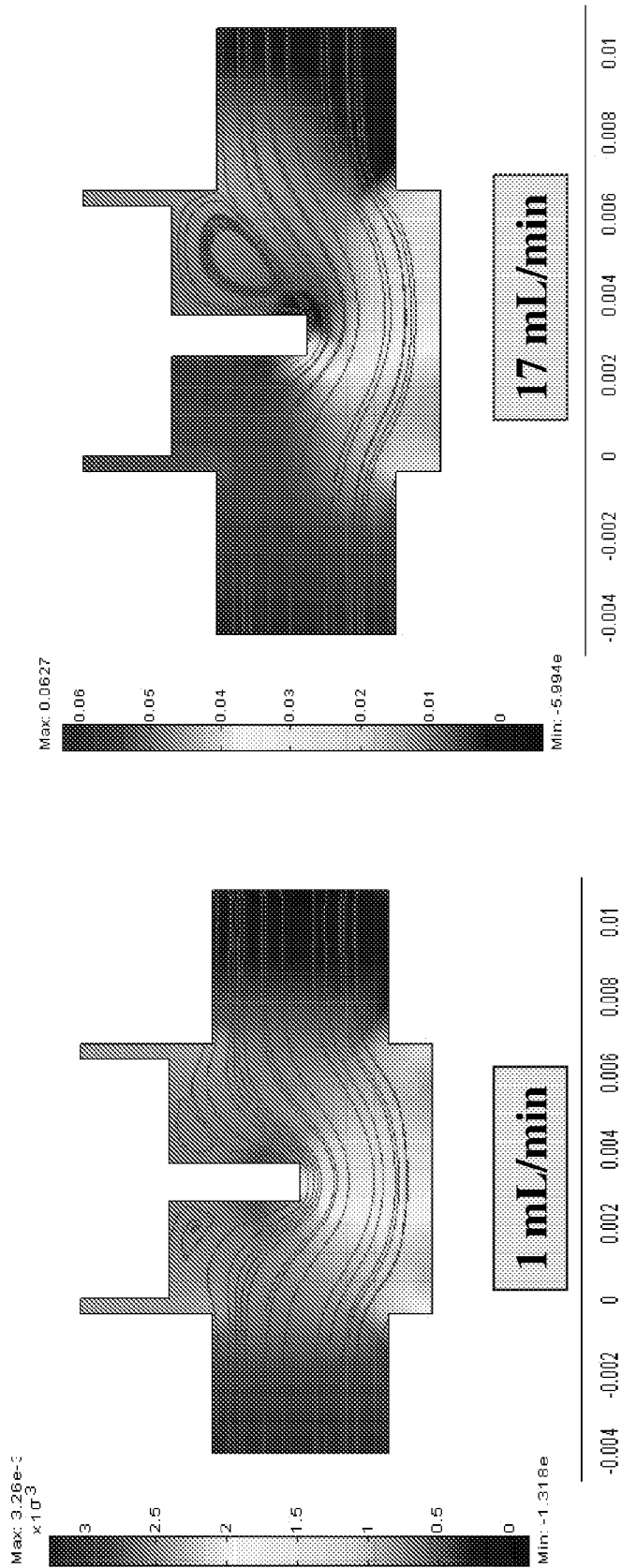
FIG. 19 is another graph illustrating a pressure map and velocity field in a flow cell at the various flow rates.

FIG. 19 illustrates surface plots 98 and 100 of SFC-1 wherein the width of the sensor was placed parallel (as depicted in FIG. 9) to inflow, for flow rates of 1 mL/min and 17 mL/min, respectively. Unlike the perpendicular case, two re-circulation regions developed on both sides of the sensor even at a low flow rate of 1 mL/min. As the flow rate was increased, the re-circulating region decreased on the inflow side, and the one on the outlet side increased significantly.

Unlike SFC-1, the flows in SFC-2 showed no increase or decrease in the size of the re-circulating region in the flow rate range investigated. This is illustrated in FIG. 20. FIG. 20 illustrates surface plots 102 and 104, of SFC-2 wherein the width of the sensor was placed perpendicular (as depicted in FIG. 10) to inflow, for flow rates of 1 mL/min and 17 mL/min, respectively. However, as the flow rate increased, more of the inflow appeared to contact the sensor as indicated by the smaller streamline bandwidth at higher flow rate.

As depicted in region 101, the medium tends to circulate and be restricted to a confined volume. This circulation tends to reduce the opportunity of the portion of the PEMC sensor in the region 101 to come into contact with target material flowing through the flow cell. To prevent and/or mitigate this type of medium flow, in an example embodiment, the flow cell comprises a baffle 103. A baffle can be positioned at any appropriate location and in any appropriate angle. A baffle can be straight, curved, or a combination thereof. Multiple baffles can be utilized. In another example embodiment, a PEMC sensor is positioned, instead of, and at the location of the baffle 103.

In various embodiments, a mixer or stirrer can be utilized to augment medium flow. The mixer can comprise any appropriate mixer, such as a propeller-like mixer, a magnetic stirrer, or the like, for example.

Figure 21:
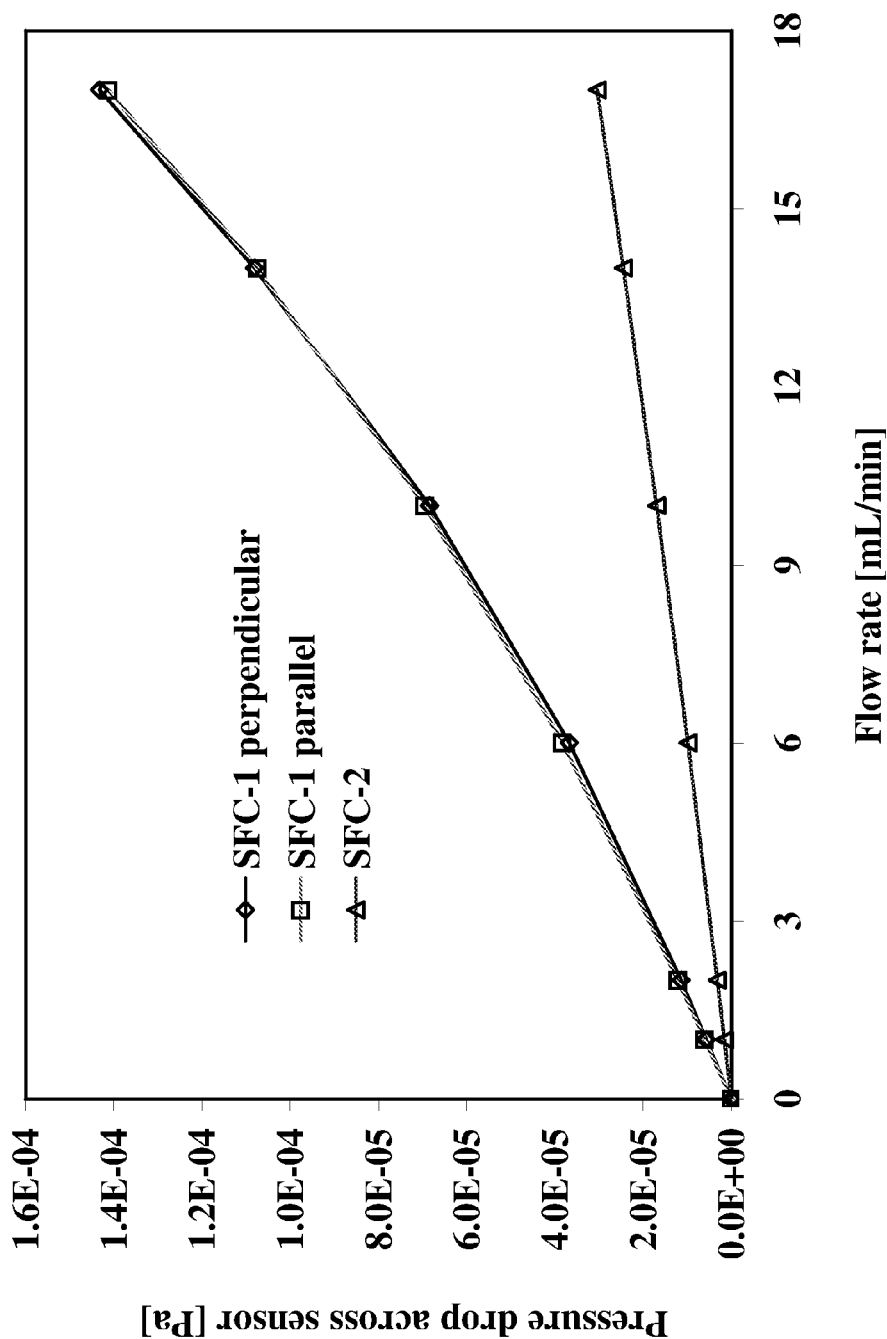
FIG. 21 is an example graph illustrating pressure drop across the PEMC sensor for various flow rates.

In order to determine the sensor response to flow rate, the pressure drop across the sensor was compared at various flow rates, and the results are plotted in FIG. 21. Note that the pressure drop across the sensor in SFC-1 was not affected significantly by the position of the sensor, and the pressure drop increased as flow rate was increased. Furthermore, the pressure map of FIG. 21 shows higher pressure acting somewhat uniformly on the inflow side of the sensor. In SFC-2 the pressure drop across the sensor increased slightly with flow rate, which may explain the observed fluctuations in resonance frequency around 217 Hz (See FIG. 16) at higher flow rates.

Figure 22:
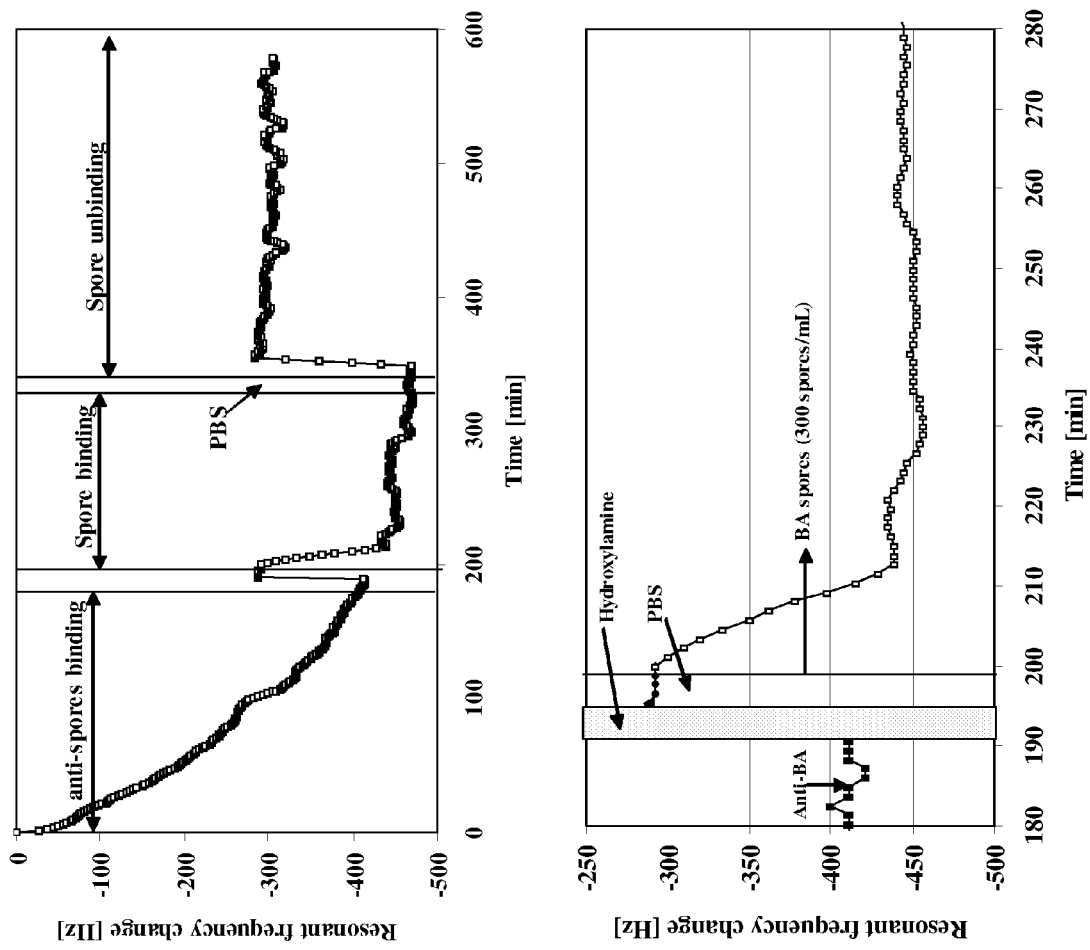
FIG. 22 is an example graph illustrating the change in the resonance frequency of a PEMC sensor in a flow cell as a function of time.

Model pathogen *Bacillus anthracis* (BA) spores at 300 spores/mL were used to evaluate the performance of a PEMC sensor in the SFC-2 design. In FIG. 22 the change in the fundamental resonance frequency as a function of time for the capture of BA spore in solution is presented. FIG. 22 shows the detection sequence including sensor preparation; namely reaction of sulfo-NHS activated anti-BA with the sensor surface amine groups, the binding of BA spores, and finally the release of the bound pathogen. The anti-BA immobilization was carried out by filling SFC-2 with PBS containing anti-BA at 10 μg/mL in stagnant conditions for approximately 3 hours. The reaction (amide bond formation) of the activated anti-BA to the aminated surface began immediately resulting in a decrease in the resonance frequency, and ultimately reaching a steady state frequency change of 420±3 Hz. In FIG. 22 the resonance frequency response from the start of the experiment is shown. Hydroxylamine was then flowed through the cell at 1 mL/min to convert activated carboxylic groups on anti-BA back to normal carboxylic groups. It can be seen in FIG. 22 that the initiation of hydroxylamine flow resulted in a step increase of 122 Hz and reached a value of −298±3 Hz, with respect to the initial value. This step response is similar to what was observed in FIG. 17. Note that immediately after the initial rapid rise, the resonance frequency decreased and reached a steady state value and remained constant, within ±3 Hz until the flow of BA spore solution was initiated.

Exposure to BA spores caused a rapid decrease in the resonance frequency. The total frequency change was 160±3 Hz and reached steady state in 20 minutes. Following the conclusion of BA spore binding, PBS was flowed at 1 mL/min for 10 minutes to rinse out SCF-2 and the tubing connections. During the PBS rinse, residues of the previous step and the weakly adsorbed antibody were removed. The change in resonance frequency was very small and was within the noise level (±5 Hz). The exposure of the sensor to release buffer (pH 2.0) caused an immediate increase of the resonance frequency and reached a constant value (300±6 Hz), which was within 2 Hz of the resonance frequency value prior to BA spore flow. These responses suggest that all the bound BA spores were released by the release buffer.

The total change in the measured resonance frequency of BA spore binding depends on the amount of antibody that is attached to the sensor, and the accessibility of spores to the binding region of the antibody. Immobilization under flow conditions consumes a 3-4 times larger amount of antibody at a given concentration. If higher effective surface concentration is achieved, higher sensitivity to BA spore detection is a likely outcome and is desirable. FIG. 23 shows the frequency change of the measured resonance peak for the attachment of anti-BA and the corresponding binding of BA spores both in stagnant conditions and under flow conditions. The measured resonance frequency change for the reaction of anti-BA (10 μg/mL) to the aminated sensor surface is presented in graph 106. In stagnant conditions the steady state value of the measured resonance frequency change (230 Hz) was lower than that observed under 1 mL/min flow conditions (430 Hz). Clearly, flow enhances transport of activated antibody to the sensor surface resulting in a higher level of binding. Also, the rate of frequency change was higher under flow conditions suggesting higher anti-BA immobilization on sensor surface.

In graph 108, stagnant and flow modes were compared in flow cell SFC-2 for the binding of BA spores (300 spores/mL) to the sensor surface. Once again, flow increases the attachment kinetics. It took 10 minutes to reach 71% of the total frequency response under flow conditions compared to 26% of the total frequency response reached under stagnant measurement conditions. The initial rate at which the resonance frequency changed was also higher in flow suggesting an increase in spore attachment kinetics. One key observation of the results presented here is that the steady state frequency values for both anti-BA and the corresponding BA spore binding were approximately 100% higher under flow conditions as compared to stagnant conditions.

In order to examine the influence of flow with regard to detection of protein molecules a model protein, bovine serum albumin (BSA), was chosen. BSA was sequentially attached and released as shown in FIG. 24. The sensor was initially exposed to anti-BSA (100 μg/mL) to immobilize the sensing molecule. The fundamental resonance frequency (23 kHz in air) was monitored for 2 hours under stagnant conditions and the results given in FIG. 24 (labeled anti-BSA) show that the resonance frequency decreased by approximately 900±5 Hz. This value is higher in comparison to anti-BA, and is due to the higher concentration of anti-BSA used. Initiation of flow (1 mL/min) resulted in a step increase of resonance frequency. Flowing of solution containing BSA (labeled as BSA-1 in FIG. 24) caused a rapid initial decrease followed by an exponential decrease, and finally reached a steady state resonance frequency value of 396±10 Hz.

The release of the bound BSA was carried out with release buffer (PBS/HCl, pH 2.0), labeled as HCl-1 in FIG. 24. Exposure of the BSA-bearing sensor to release buffer caused an immediate rise in the resonance frequency and the frequency reached a constant value at the same value that was present prior to BSA exposure. This suggests that the mass of BSA that was bound to the sensor was removed successfully without apparently destroying the underlying antibody layer. As a result the sensor was exposed to BSA again, labeled as BSA-2 in FIG. 24. The resonance frequency decreased and reached a steady state value of 1137±5 Hz, with a total change in frequency of 393±5 Hz, indicating that the antibody was fully regenerated without any loss of antibody activity. However, regenerating the surface the second time (labeled as HCl-2 in FIG. 24) resulted in a higher resonance frequency change than that was observed during the first regeneration suggesting that some of the antibody may have been released. The release profile, HCl-2, is also slightly different from HCl-1. In light of these results it is reasonable to suggest that PEMC sensors can be re-used a limited number of times.

The sensor frequency response can be expressed as:

$$(\Delta f)=(\Delta f_{\infty})(1-e^{-k_{obs}\tau}) \quad (3)$$

where (Δf) is the change in resonance frequency at time, τ, and ($\Delta f_{\infty}$) is the steady state resonance frequency change. $k_{obs}$ is the observed binding rate constant and is linearly dependent on concentration. Eq. (3) can be rearranged as:

$$\ln\left(\frac{(\Delta f_{\infty})-(\Delta f)}{(\Delta f_{\infty})}\right)=-k_{obs}\tau \quad (4)$$

The model is based on the assumption that the bulk concentration $C_{b0}$ remains constant during a detection episode. Equation (4) suggests that the observed binding rate constant $k_{obs}$ can be determined from a plot of the left hand side (LHS) versus τ.

The kinetic approach employed is the initial rate analysis of the frequency response data to obtain the observed binding rate constant, $k_{obs}$ using Equation (4). At time close to zero there are no concentration gradients, and thus diffusion effects are absent. This is useful when one deals with low concentration analyte. Furthermore, the bulk concentration of antibody and antigen are known accurately. Therefore, limiting the initial rate analysis to the first ten minutes is a reasonable approach to obtain the kinetic constant.

Antibody reaction with primary amines on glass results in covalent bonds and therefore, the binding can be modeled as an irreversible reaction. The exponential decay of the measured resonance frequency changes in both the stagnant and flow measurements of the antibody-amine reaction provides useful kinetics information (see graph 106 of FIG. 23). Fitting the sensor response presented in FIG. 22 to equation (4) gave straight lines with excellent correlation coefficients of 0.96 and 0.92 for the stagnant and flow methods, respectively, and is illustrated in graph 110 of FIG. 25. The slope of each line of graph 110 gives the observed characteristic binding rate constant, $k_{obs}$. The binding rate constant for anti-BA under stagnant and flow conditions were 0.042±0.008 $min^{-1}$ and 0.213±0.05 $min^{-1}$, respectively. It is clear from $k_{obs}$ values that flow causes approximately a five-fold increase in the characteristic observed rate constant. The higher binding rate observed in the flow modality may be explained by enhanced transport of anti-BA to the sensor surface.

The experimental data of BA spores were analyzed in the same fashion as anti-BA (see FIG. 25 graph 112) and a summary of the analysis is given in Table 1 below. Again, the characteristic sensor response rate constant, $k_{obs}$, is higher in the flow measurement modality. The observed binding rate constants were 0.195±0.02 $min^{-1}$ and 0.263±0.05 $min^{-1}$, respectively, for stagnant and flow conditions. The kinetic rate analysis suggests that binding of the pathogen can be achieved in a shorter time (about 10%) under flow conditions.

TABLE 1 k$_{obs}$ values of anti-BA, BA, and BSA under stagnant and flow conditions.

| Sample | k$_{obs}$ values in stagnant (min$^{-1}$) | k$_{obs}$ values in flow (min$^{-1}$) |
| --- | --- | --- |
| Anti-BA | 0.042 ± 0.008 | 0.213 ± 0.05 |
| BA | 0.195 ± 0.02 | 0.263 ± 0.05 |
| BSA-1 | — | 0.111 ± 0.006 |
| BSA-2 | — | 0.103 ± 0.005 |

Figure 24:
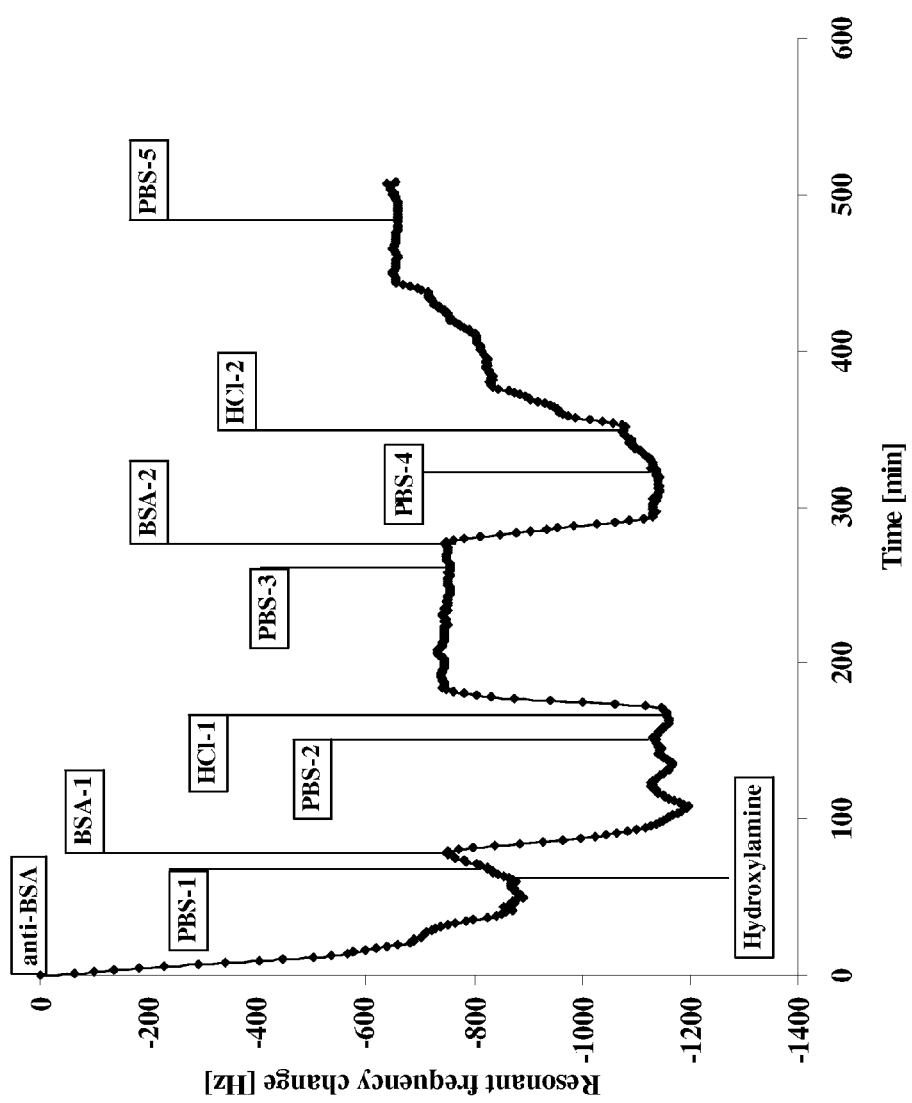
FIG. 24 is yet another example graph illustrating the change in the resonance frequency of a PEMC sensor in a flow cell as a function of time.
Figure 25:
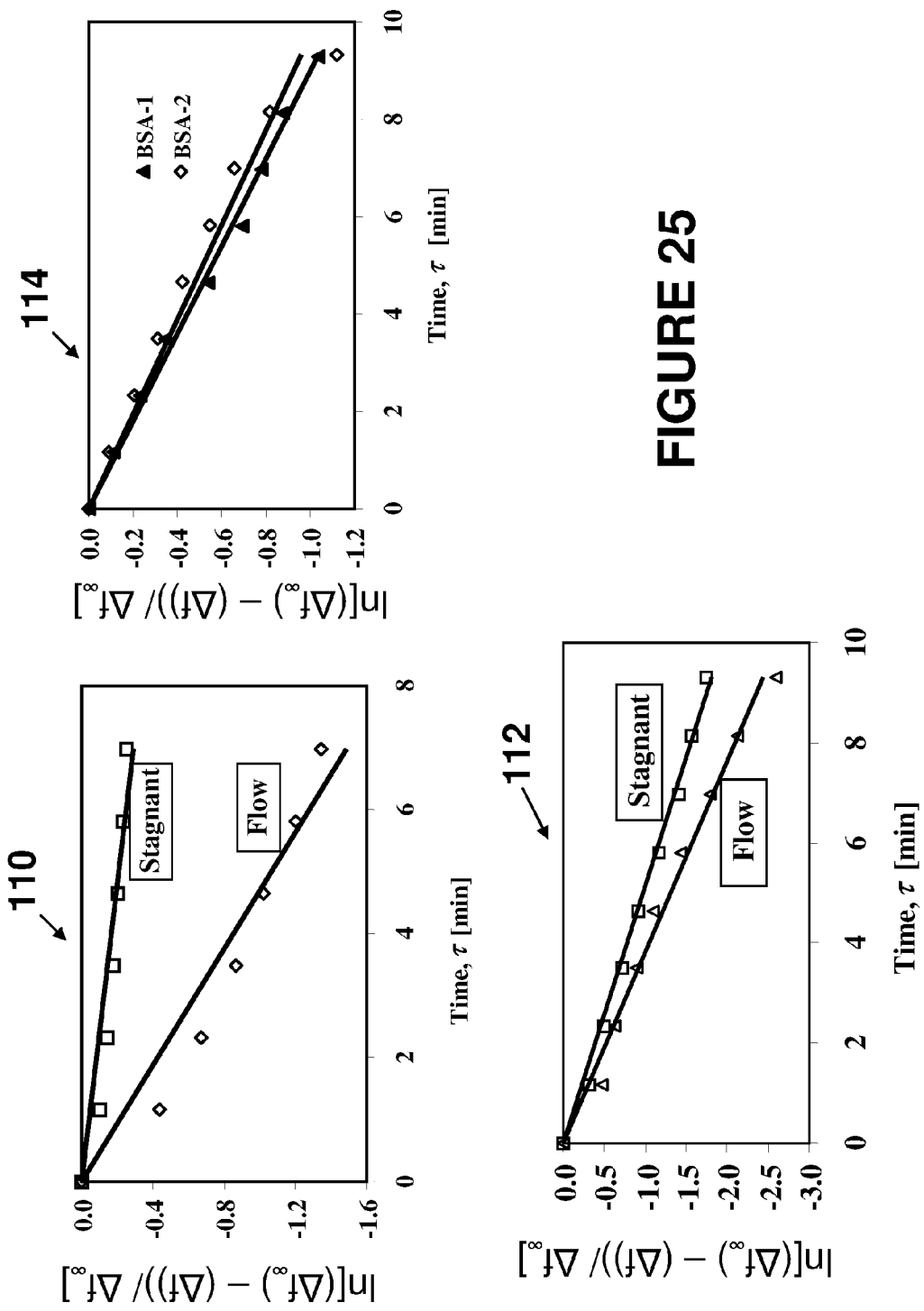
FIG. 25 is an example graph illustrating binding rates in stagnant and flow conditions.

The binding kinetics of protein to surfaces is an important parameter in many sensor applications. However, the regeneration of the antibody surface is of great interest since it determines the status of the bound antibody. Fitting the frequency response data for BSA binding presented in FIG. 24 (initial binding (BSA-1) and after regeneration (BSA-2)) to equation (4) the observed rate constants, k$_{obs}$ were determined to be 0.111±0.006 min$^{-1}$ and 0.103±0.005 min$^{-1}$, respectively. See kinetic analysis in FIG. 25 graph 112. These results suggest that there was only a small loss in the antibody activity after the first surface regeneration with release buffer pH 2.0.

The above experiment indicates that flow cell configured for a PEMC sensor functionalized with the appropriate antibody can be used to detect low concentrations of proteins and pathogens in real time. Sensor response was rapid for spore detection and for protein binding. Furthermore, the total sensor response was significantly higher (about 100%) for both *Bacillus anthracis* spores and protein (BSA) under 1 mL/min flow conditions compared to stagnant conditions.

In another experiment, the detection of *Escherichia coli* (hereinafter "EC") O157:H7 at 1 cell/mL in batch, with increasing flow rate, and at very high flow rate was demonstrated. The infectious dosage of *E. coli* O157:H7 has been reported as 10 cells and the United States Environmental Protection Agency standard for drinking water is 40 cells per liter. This experiment employed three approaches for the detection of EC at 1 cell/mL using piezoelectric-excited millimeter-sized cantilevers: first a batch configuration, second a progressive increase in flow rate, and finally a flow and stop measurement at very high flow rate. Flow, of the sample, was used to improve contact of the pathogen with the sensor as the pathogen count was very low. The batch experiments were carried out with 1 EC in 1 mL of buffer, while the flow experiments were done using a 1 liter sample buffer containing 1000 EC.

In this experiment the use of multiple resonance peaks in the detection of *E. coli* O157:H7 is demonstrated. Because the data acquisition program did not have the capability to simultaneously monitor multiple resonance peaks, the experiment was carried out in a flow and stop modality. That is, the sample solution was flown for a 5 minutes period and then stopped, followed by the monitoring of each resonance peak until it stabilized. The sample volume was 1 liter and the EC sample (1 cell/mL) was flowed at a rate of 17 mL/min. Therefore, the sensor's frequency response for several resonance modes was characterized by a constant mass each time. Furthermore, the frequency response gives a measure of the sensitivity of the various peaks. An the other hand, a non-flow condition ensures that the measured resonance frequency changes were not due to flow, but only due to changes in mass caused by EC attachment.

In this experiment, it was shown that an increase in flow rate increased the attachment of pathogen to an anti-body functionalized PZT-anchored piezoelectric-excited millimeter-sized cantilever (PAPEMC) sensor. The initial rate of attachment and the total sensor response also increases with flow rate. In addition, the time to reach a steady state frequency value increased with flow rate. PAPEMC sensors were shown to be mechanically robust and to have the sensitivity to detect pathogen at 1 cell per milliliter in real time.

Figure 26:
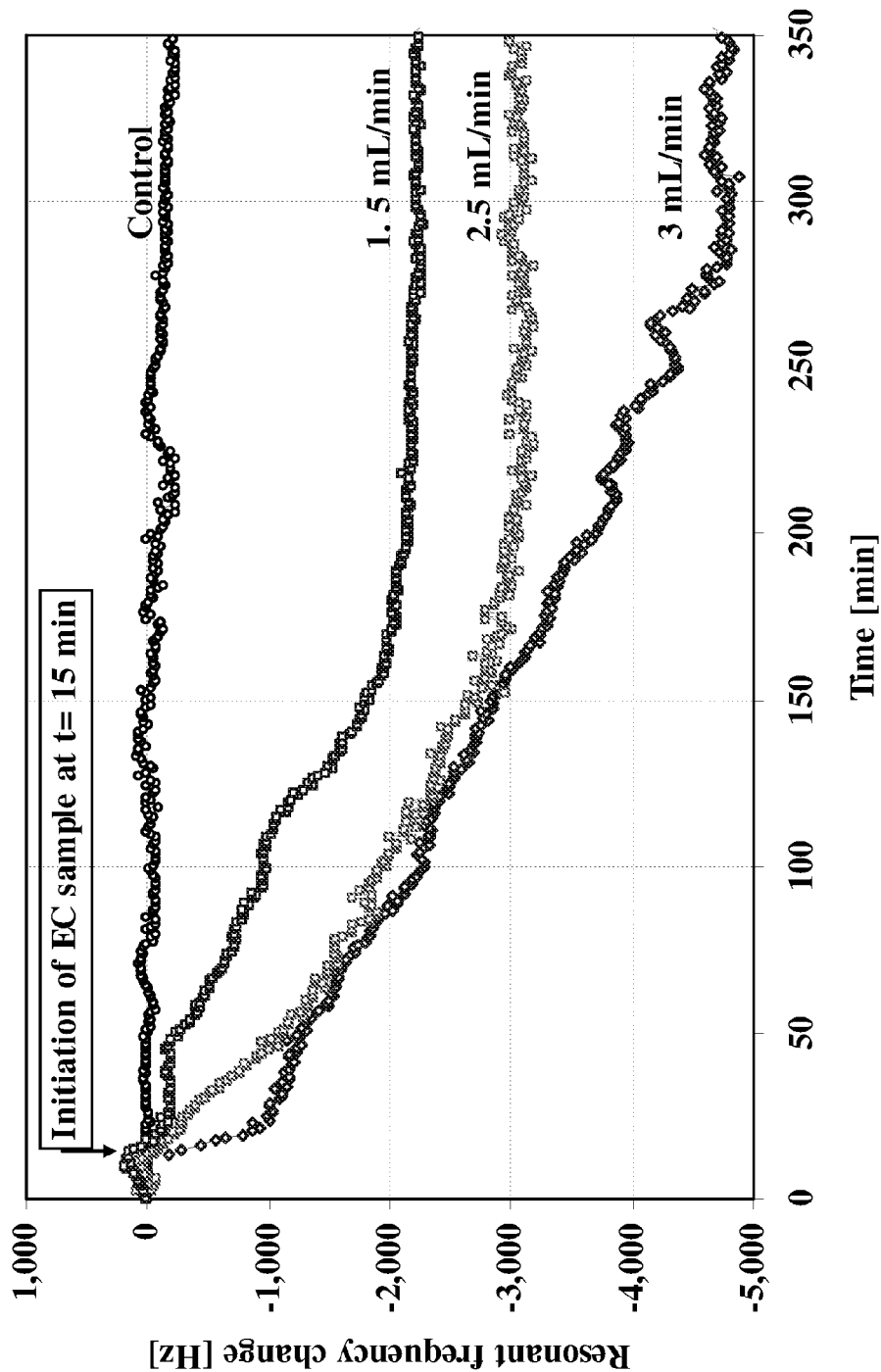
FIG. 26 is an example graph illustrating PEMC sensor response at 800 kHz under full liquid immersion, due to the binding of *Escherichia coli* at various flow rates.

In another experiment, a PEMC sensor was immobilized with antibody specific to EC O157:H7 was used to detect EC at 1 cell per mL. The PEMC sensor configuration was as shown in FIG. 5 and the SFC configuration was as shown in FIG. 10. The response at 800 kHz under full liquid immersion, due to the binding of EC at various flow rates is depicted in FIG. 26. The freshly prepared antibody-functionalized sensor was exposed to a 1L sample of EC at 1 cell/mL and sample flow rates of 1.5, 2.5, and 3 mL/min. In all the experiments, the PEMC sensor responded with an initial rapid decrease in resonant frequency, followed by a slower decrease until the frequency reached a steady state value. The rate of EC binding and the total resonant frequency change increased with increasing flow rate. The steady state frequency changes for the binding of EC (1 cell/mL) at 1.5, 2.5, and 3 mL/min were 2,230±11, 3,069±47, and 4,686±97 Hz, respectively. The standard deviation indicated is the variation in resonant frequency at steady state over a period of 10 minutes. The time to reach steady state is a function of the flow rates used. The steady state frequencies at 1.5, 2.5, and 3 mL/min were achieved in 192, 230, and 290 minutes, respectively. Since the number of EC cells in each of the sample was the same, we conclude that the increased flow rate improved contact of EC to the sensor. At each flow rate a control experiment was also carried out. The control was an antibody functionalized cantilever exposed to PBS buffer at a flow rate that was the same as in the detection experiment. The control response shown in FIG. 26 was carried out at 3 mL/min. The resonant frequency decreased slightly 77±81 Hz, which for practical purposes is within the noise level we observed with cantilevers of this design. The data shown in FIG. 26 suggest that PEMC sensors have the sensitivity to detect EC at 1 EC/mL in the flow configuration used.

Figure 27:
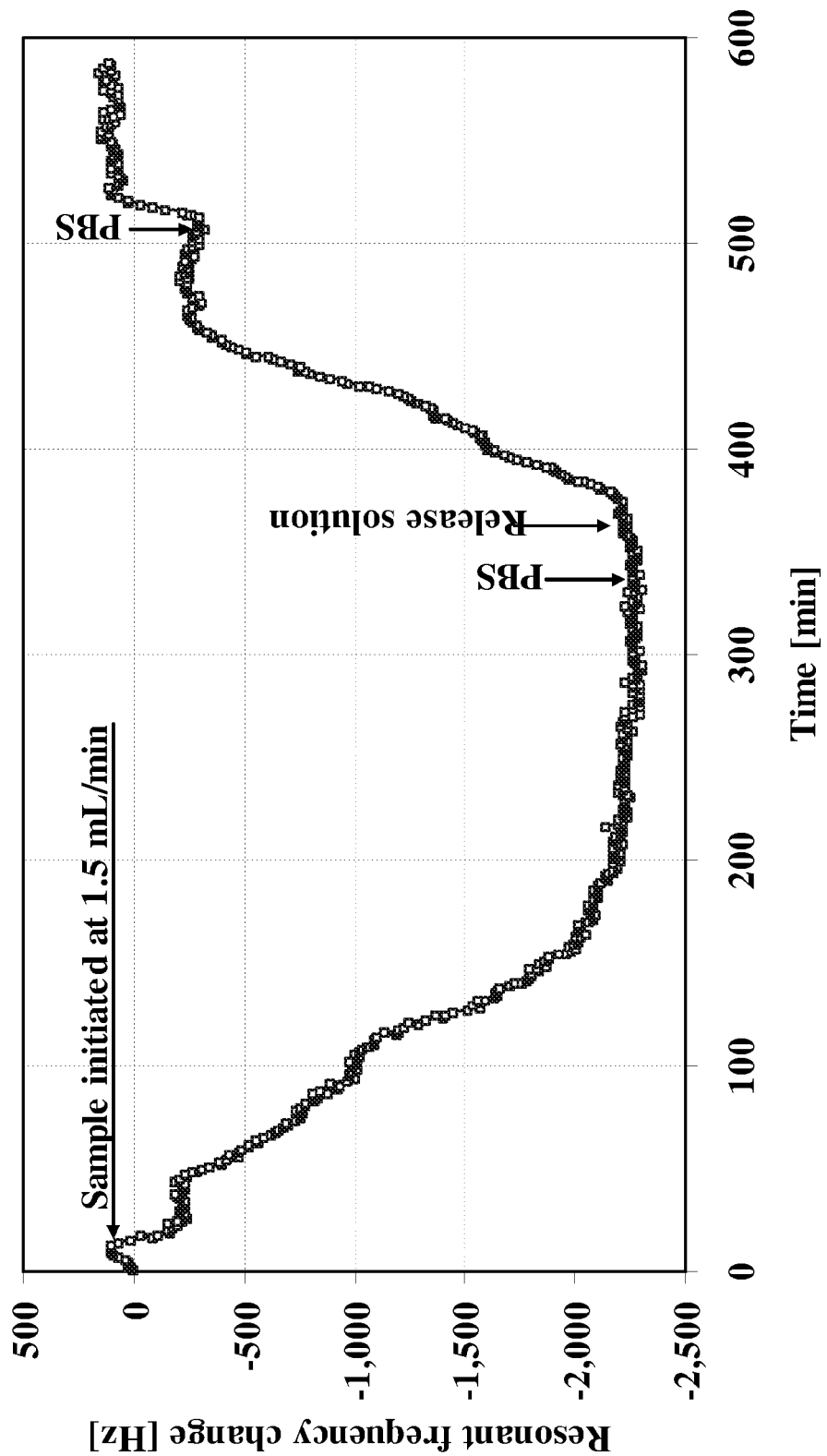
FIG. 27 is an example graph illustrating the attachment and release sensor response for bound *Escherichia coli* at 1.5 mL/min.

To confirm that the observed sensor response was indeed due to the binding of EC, in each experiment, after completion of the detection segment, the flow circuit was rinsed with PBS followed by exposing the sensor to a pH 2.02 solution, and finally PBS was re-introduced to return the sensor to the environment that was present prior to EC attachment. FIG. 27 shows the attachment and release sensor response for the bound EC at 1.5 mL/min. Upon initiation of the sample flow the sensor's resonant frequencies decreased monotonically by 2,230±11 Hz. After reaching steady state, PBS was pumped through the flow-cell for 30 minutes followed by a pH 2.02 solution made from PBS and hydrochloric acid (HCl). The PBS-rinse did not show any noticeable change in frequency. In fact, the frequency increased by only 30 Hz, which is lower than the response of the control. On the other hand, exposure of the sensor to the release solution resulted in an immediate increase in frequency and reaching a constant frequency change of 1,905±17 Hz. The total frequency change obtained during the release was less than that of the attachment response; which may be due to the slightly higher density of the release solution. Flushing the SFC with PBS afterwards caused a further increase in the resonant frequency by 392±20 Hz, indicating that the liquid environment prior to the release was re-established. In addition, the final frequency change reached was approximately 110 Hz higher than the value before initiation of the EC sample.

Because the resonance characteristics of PEMC sensors can be unstable under high liquid flow rates (17 mL/min), an experiment was conducted in a flow-stop-measure modality. Detecting EC in a flow and stop modality resulted in multiple resonant peaks in the detection of EC. The sample volume was 1 liter and the EC sample (1 cell/mL) flow rate was at 17 mL/min. The behavior of the sensor's three higher-order resonant modes by a constant mass was also measured. The frequency response provides a measure of the sensitivity of the various peaks. In addition, a non-flow condition ensures that the measured resonant frequency changes were not due to flow effects, and only mass changes caused by EC attachment.

Figure 28:
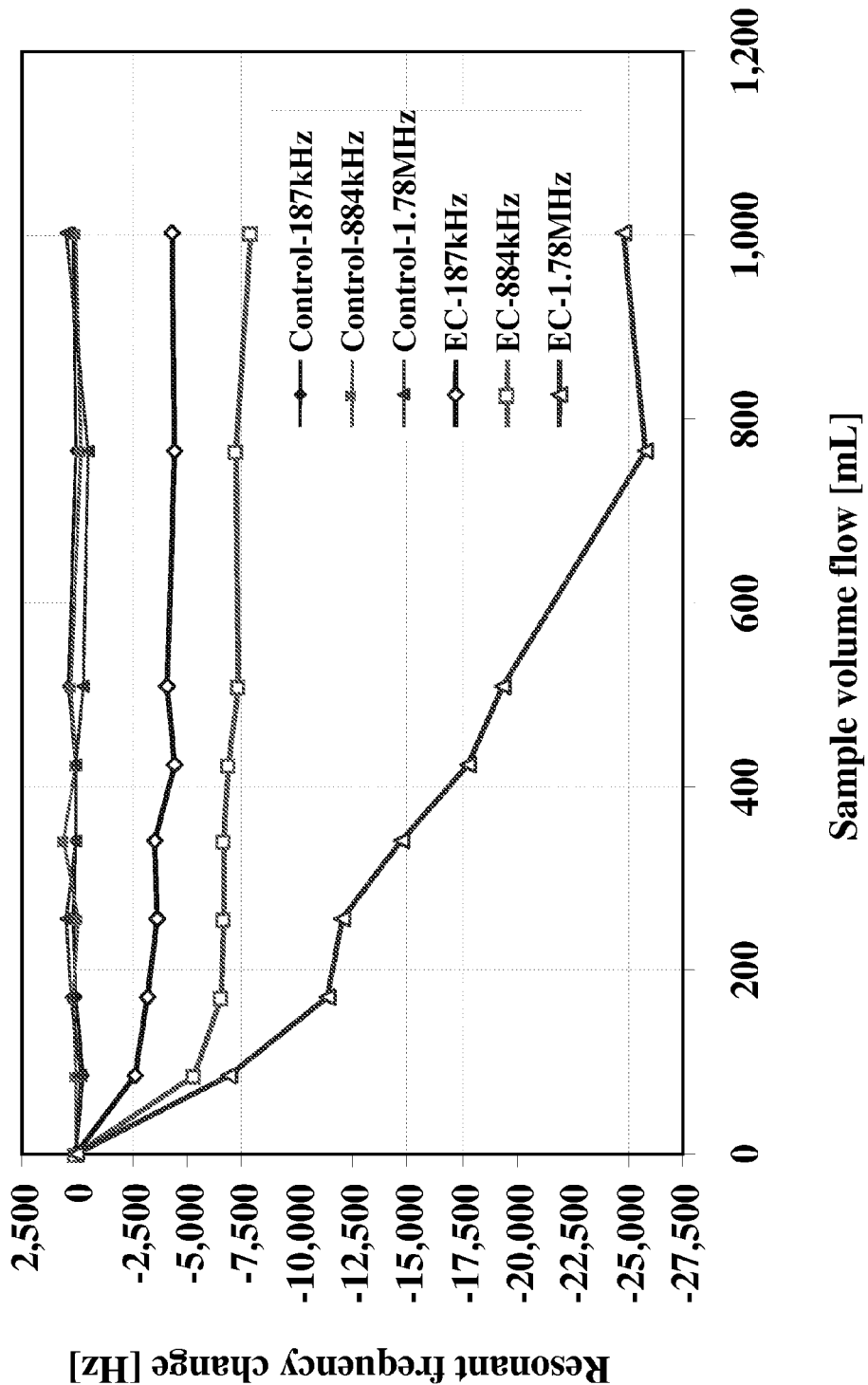
FIG. 28 is an example graph illustrating resonance frequency changes as a function of volume flow for *Escherichia coli* immersed in liquid.

In FIG. 28, the 162.5, 800.0, and 1,725.5 kHz resonant peaks, under liquid immersion, were used in detection. The plot shows the frequency response of the sensor versus the sample volume that flowed through the SFC prior to resonant frequency measurement. The sample was flowed for 5 minutes, stopped, and then the resonant frequencies of the three modes were monitored individually until they stabilized, which typically took place in 5 to 10 minutes. This step was repeated until the sample volume was completely pumped through the SFC. As shown in FIG. 28, the resonant frequencies of the different modes decreased rapidly after the initial 5 minutes of sample flow (sample volume of 85 mL) and ultimately reached a steady state frequency change of 4,340±49, 7,188±52, and 25,850±63 Hz corresponding to the 162.5, 800.0, and 1725.5 kHz resonant modes under liquid immersion. The significance of these results is that for the same mass change the various resonant modes responded to different extent. Given that the noised levels were approximately similar, the 1,725.5 kHz mode exhibited the highest sensitivity of the modes examined. That is, the frequency change per pathogen detected was approximately 26 Hz/pathogen. Along with each detection experiment a control experiment was also conducted in the same fashion. The control experiment conducted with an antibody-functionalized PEMC sensor exposed to PBS buffer yielded resonant frequency values that fluctuated at 56±154, 97±225, and 21±328 Hz for the 162.5, 800.0, and 1,725.5 kHz modes, respectively. These results indicate that the cantilever is mechanically robust and at the same time very sensitive.

In another experiment, attempts to shorten detection time were investigated. Airborne *Bacillus anthracis* (BA) spores were detected. Airborne (BA) spores were obtained by air sampling and then exposing the collected sample to an antibody-functionalized PEMC sensor. Using a commercial air sampler, a 10-minute air sample at 267 liters/min captured the airborne particulates containing (BA) spores and concentrated them into 5 mL of phosphate buffered saline (PBS). This sample was then injected into a flow cell containing an antibody-functionalized PEMC sensor. The flow cell was configured as depicted in FIG. 10 and the PEMC sensor was configured as depicted in FIG. 5. The resonant frequency of the PEMC sensor at 925.1 kHz decreased exponentially as the BA spores attached to the sensor surface producing a positive response well beyond the noise level in 2 minutes and reached a steady state value in 20 minutes. Results indication that the detection of 38 BA spores per liter of air is achievable in near real-time with an estimated lower limit of detection of approximately 5 spores per liter of air in the configuration tested.

Figure 29:
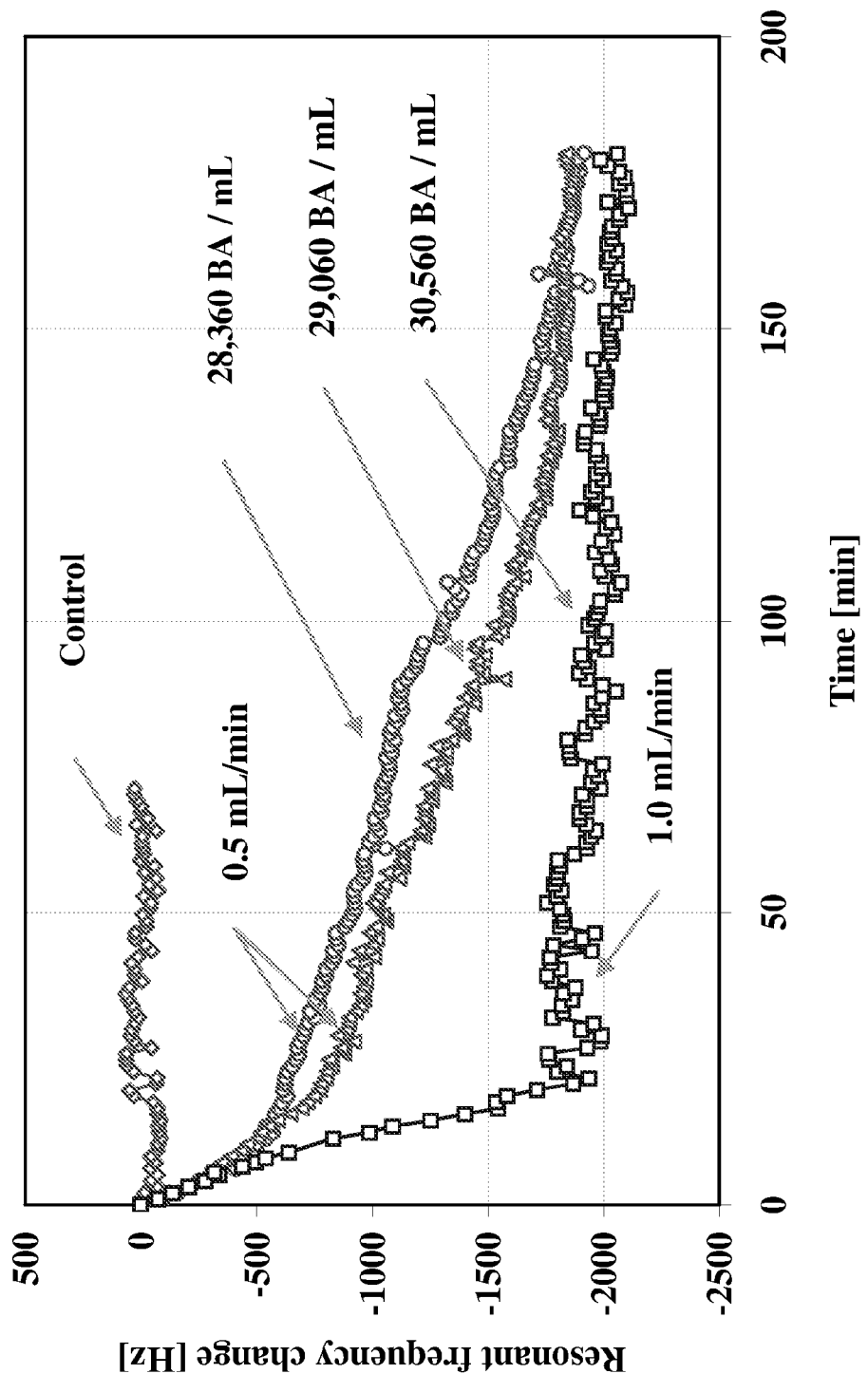
FIG. 29 is an example graph illustrating resonance frequency change as a function of time for *Bacillus Anthracis* spores.

Detection time was shortened by increasing flow rates. Flow rate was set at 0.5 and 1.0 mL/min for 3 separate runs at a nominal spore concentration of 35,000 BA/mL (34,100 to 36,000) plus control at zero BA/mL. The control was an antibody-functionalized PEMC sensor exposed at 1 mL/min to the control PBS buffer that was taken from the SASS 2000. FIG. 29 depicts the results of these experiments where experiments 1 and 2 were carried out at 0.5 mL/min and experiment 3 at 1.0 mL/min. In the experiments depicted in FIG. 29, the sample was recirculated. By recirculating the sample, spore attachment is increased. The resonance frequency changed as a function of time to the binding of BA spores at different flow rates to the final steady-state value. For samples from experiments 1 and 2, flow rate of 0.5 mL/min and for sample from experiment 3, 1 mL/min was used. The three samples contained approximately the same BA concentration. Although the total resonant frequency changes are similar, the binding rate was more rapid at the higher flow rate. As shown in FIG. 29, the time to reach steady state frequency decreased by approximately 80%. The higher the flow rate used, the more the transport of spores to the sensor surface was enhanced. At higher flow rates, the signal-to-noise ratio decreased, and thus the flow rate was limited to 1 mL/min in these experiments. In an example embodiment, the stop and flow modality can be utilized to obtain resonance frequency measurements. That is rapid flow can be followed by stoppage for resonance frequency measurement. Such a method further reduces the sensor response time.

In FIG. 29, the three experiments containing nearly the same number of spores (29,330±1,120 per mL) gave nearly the same PEMC sensor response of 1957±129 Hz. The maximum noise level of measurement in these three experiments was 53 Hz and thus the variance of sensor response for the three samples is less than three times the noise level. That is, the PEMC sensor provides repeatable measurement considering the fact that in each experiment, the sensor surface was prepared starting with cleaning followed by amination and fresh antibody immobilization. In accordance with the results depicted in FIG. 29, it is deduced that 1 mL/min SFC flow rate reduces detection time while not affecting the steady state response significantly. Hence, subsequent detection experiments were conducted at 1 mL/min.

In accordance with various experiments conducted on airborne BA spores, an air sampler and a PEMC sensor can be utilized to measure airborne BA spores in less than 30 minutes; 10 minutes for particulate capture by the air sampler and less than 20 minutes for total PEMC sensor response. The time for positive indication of the presence of BA is less than 12 minutes.

While illustrative embodiments of flow cells configured for PEMC sensors have been described herein, it is to be understood that other similar embodiments can be used or modifications and additions can be made to the described embodiment of flow cells configured for PEMC sensors without deviating therefrom. Therefore, flow cells configured for PEMC sensors should not be limited to any single embodiment, but rather should be construed in breadth and scope in accordance with the appended claims.

What is claimed:
1. A flow cell comprising:
  a first aperture configured to allow a medium to flow into a reservoir portion of the flow cell;
  a second aperture configured to allow the medium to flow out of the reservoir portion of the flow cell; and
  the reservoir portion, wherein:
    the reservoir portion is configured to contain therein at least a portion of the medium;
    the reservoir portion contains at least a portion of a sensing surface of a piezoelectric-excited millimeter-sized cantilever (PEMC) sensor;
    the PEMC sensor comprises:
      a piezoelectric layer comprising a proximate end and a distal end;

a non-piezoelectric layer comprising a proximate end and a distal end, wherein at least a portion of the piezoelectric layer is coupled to at least a portion of the non-piezoelectric layer such that the piezoelectric layer and the non-piezoelectric layer are not coextensive;

a base portion coupled to the proximate end of the piezoelectric layer, wherein the base portion is not attached to the proximate end of the non-piezoelectric layer; and electrodes operatively associated with the piezoelectric layer;

at least a portion of the medium in the reservoir portion is exposable to the sensing surface of the PEMC sensor; and exposure of the medium to the sensing surface of the PEMC sensor is enhanced under flow conditions as compared to the medium being static within the flow cell.

2. A flow cell in accordance with claim 1, further comprising a plurality of apertures configured to allow the medium to flow into the reservoir portion of the flow cell.

3. A flow cell in accordance with claim 1, further comprising a plurality of apertures configured to allow the medium to flow out of the reservoir portion of the flow cell.

4. A flow cell in accordance with claim 1, wherein:
the first aperture is positioned on a side of the reservoir portion of the flow cell;
the second aperture is positioned on an opposite side of the reservoir portion of the flow cell; and
the sensing portion of the PEMC sensor is positioned between the first aperture and the second aperture.

5. A flow cell in accordance with claim 1, wherein:
the first aperture is positioned on a side of the reservoir portion of the flow cell;
the second aperture is positioned on a bottom of the reservoir portion of the flow cell; and
the PEMC sensor is positioned between the first aperture and the second aperture.

6. A flow cell in accordance with claim 1, wherein a length of the non-piezoelectric layer is in a range of about 0.1 mm to about 10.0 mm.

7. A flow cell in accordance with claim 1, wherein a length of the piezoelectric layer is in a range of about 0.1 mm to about 10.0 mm.

8. A flow cell in accordance with claim 1, wherein a width of the non-piezoelectric layer is in a range of about 0.1 mm to about 4.0 mm.

9. A flow cell in accordance with claim 1, wherein a width of the piezoelectric layer is in a range of about 0.1 mm to about 4.0 mm.

10. A flow cell in accordance with claim 1, wherein the medium comprises at least one of a liquid and a gas.

11. A flow cell in accordance with claim 1, wherein the flow cell and the PEMC sensor form a single integrated entity.

12. A flow cell in accordance with claim 1, wherein the PEMC sensor is detachable from the flow cell.

13. A flow cell in accordance with claim 1 further comprising at least one baffle within the reservoir portion.

14. A flow cell in accordance with claim 1, further comprising a stirrer configured to stir the medium.

15. A flow cell in accordance with claim 1, the flow cell further configured to receive a plurality of PEMC sensors.

16. A flow cell in accordance with claim 15, wherein:
at least one of the plurality of PEMC sensors is configured to attract a first target material;
at least one of the plurality of PEMC sensors is configured to attract a second target material; and
the first target material differs from the second target material.

17. A flow cell in accordance with claim 15, wherein at least one of the plurality of PEMC sensors is configured as a control sensor.

18. A method for detecting a target material, the method comprising:
causing a medium to flow in a reservoir portion of a flow cell configured to receive a piezoelectric-excited millimeter-sized cantilever (PEMC) sensor, the flow cell comprising:
a first aperture configured to allow the medium to flow into a reservoir portion of the flow cell;
a second aperture configured to allow the medium to flow out of the reservoir portion of the flow cell; and
the reservoir portion, wherein:
the reservoir portion is configured to contain therein at least a portion of the medium;
the reservoir portion contains at least a portion of a sensing surface of the PEMC sensor;
the PEMC sensor comprises:
a piezoelectric layer comprising a proximate end and a distal end;
a non-piezoelectric layer comprising a proximate end and a distal end, wherein at least a portion of the piezoelectric layer is coupled to at least a portion of the non-piezoelectric layer such that the piezoelectric layer and the non-piezoelectric layer are not coextensive;
a base portion coupled to the proximate end of the piezoelectric layer, wherein the base portion is not attached to the proximate end of the non-piezoelectric layer; and
electrodes operatively associated with the piezoelectric layer;
at least a portion of the medium in the reservoir portion is exposable to the sensing surface of the PEMC sensor; and
exposure of the medium to the sensing surface of the PEMC sensor is enhanced under flow conditions as compared to the medium being static within the flow cell measuring a resonance frequency of the PEMC sensor;
comparing the measured resonance frequency with a baseline resonance frequency;
when the measured resonance frequency differs from the baseline resonance frequency, determining that a target material is present in the medium.

19. A method in accordance with claim 18, wherein the resonance frequency of the PEMC sensor is measured under flow conditions.

20. A method in accordance with claim 18, further comprising:
stopping flow of the medium; and
measuring the resonance frequency of the PEMC sensor while the flow of the medium is stopped.

21. A method in accordance with claim 18, further comprising determining an amount of target material accumulated on the sensor in accordance with a difference between the measured resonance frequency and the baseline resonance frequency.

22. A method in accordance with claim 18, further comprising rotating the PEMC sensor about a longitudinal axis of the PEMC sensor for causing target material to attach to the sensing surface.

23. A method in accordance with claim 18, wherein the flow cell comprises a plurality of apertures configured to allow the medium to flow into the reservoir portion of the flow cell.

24. A method in accordance with claim 18, wherein the flow cell comprises a plurality of apertures configured to allow the medium to flow out of the reservoir portion of the flow cell.

25. A method in accordance with claim 18, wherein:
the first aperture is positioned on a side of the reservoir portion of the flow cell;
the second aperture is positioned on an opposite side of the reservoir portion of the flow cell; and
the sensing portion of the PEMC sensor is positioned between the first aperture and the second aperture.

26. A method in accordance with claim 18, wherein:
the first aperture is positioned on a side of the reservoir portion of the flow cell;
the second aperture is positioned on a bottom of the reservoir portion of the flow cell; and
the PEMC sensor is positioned between the first aperture and the second aperture.

27. A method in accordance with claim 18, wherein a length of the non-piezoelectric layer is in a range of about 0.1 mm to about 10.0 mm.

28. A method in accordance with claim 18, wherein a length of the piezoelectric layer is in a range of about 0.1 mm to about 10.0 mm.

29. A method in accordance with claim 18, wherein a width of the non-piezoelectric layer is in a range of about 0.1 mm to about 4.0 mm.

30. A method in accordance with claim 18, wherein a width of the piezoelectric layer is in a range of about 0.1 mm to about 4.0 mm.

31. A method in accordance with claim 18, wherein the medium comprises at least one of a liquid and a gas.

32. A method in accordance with claim 18, wherein the flow cell and the PEMC sensor form a single integrated entity.

33. A method in accordance with claim 18, wherein the PEMC sensor is detachable from the flow cell.

34. A method in accordance with claim 18, wherein the flow cell further comprises at least one baffle within the reservoir portion.

35. A method in accordance with claim 18, wherein the flow cell further comprises a stirrer configured to stir the medium.

36. A method in accordance with claim 18, the flow cell further configured to receive a plurality of PEMC sensors.

37. A method in accordance with claim 36, wherein:
at least one of the plurality of PEMC sensors is configured to attract a first target material;
at least one of the plurality of PEMC sensors is configured to attract a second target material; and
the first target material differs from the second target material.

38. A method in accordance with claim 36, wherein at least one of the plurality of PEMC sensors is configured as a control sensor.

* * * * *